United States Patent [19]

Mori et al.

[11] Patent Number: 4,826,818
[45] Date of Patent: May 2, 1989

[54] PROTEINACEOUS EMULSIFIER, PROCESS FOR PREPARING SAME AND EMULSION TYPE COSMETIC COMPOSITIONS CONTAINING SAME

[75] Inventors: Kenji Mori; Kazuyoshi Morita, both of Odawara; Shizume Takemoto, Naka; Hisanao Nagasawa, Yokohama; Yasuhisa Ohtani, Hiratsuka; Masashi Matsui, Odawara; Sohichi Arai, Yokohama, all of Japan

[73] Assignee: Kanebo Ltd., Tokyo, Japan

[21] Appl. No.: 153,561

[22] PCT Filed: Oct. 26, 1984

[86] PCT No.: PCT/JP84/00512

§ 371 Date: Jun. 25, 1985

§ 102(e) Date: Jun. 25, 1985

[87] PCT Pub. No.: WO85/01890

PCT Pub. Date: May 9, 1985

Related U.S. Application Data

[63] Continuation of Ser. No. 751,775, Jun. 25, 1985, abandoned.

[30] Foreign Application Priority Data

| Oct. 26, 1983 | [JP] | Japan | 58-201823 |
| Oct. 26, 1983 | [JP] | Japan | 58-201824 |
| Feb. 20, 1984 | [JP] | Japan | 59-31269 |
| Feb. 20, 1984 | [JP] | Japan | 59-31270 |
| Aug. 28, 1984 | [JP] | Japan | 59-180177 |
| Sep. 1, 1984 | [JP] | Japan | 59-183519 |

[51] Int. Cl.$^4$ .................................. A01N 61/02
[52] U.S. Cl. .................................. 514/21; 514/773; 514/938; 514/801; 252/356; 426/586
[58] Field of Search .......... 514/2, 21, 938, 801, 514/939, 773, 774, 775; 252/356, 312; 426/602, 101, 586; 424/95, 401

[56] References Cited

U.S. PATENT DOCUMENTS

| 2,010,436 | 8/1935 | McClave | 514/938 X |
| 3,015,566 | 1/1962 | Becker | 426/602 |
| 3,431,112 | 3/1969 | Durst | 426/602 X |
| 3,582,362 | 6/1971 | Drews | 426/602 X |
| 3,712,865 | 1/1973 | Evans | 426/602 |
| 3,769,038 | 10/1973 | Mitchell et al. | 426/602 |
| 3,782,971 | 1/1974 | Van Roon | 426/602 |
| 3,927,047 | 12/1975 | Ichikawa et al. | 260/404 |
| 4,014,995 | 3/1977 | Juliano et al. | 514/938 X |
| 4,031,254 | 6/1977 | Kasik et al. | 426/602 X |
| 4,054,677 | 10/1977 | Orban | 426/602 |
| 4,217,369 | 8/1980 | Durst | 426/602 X |
| 4,235,937 | 11/1980 | Remer | 426/602 X |
| 4,298,625 | 11/1981 | Cillario | 426/602 X |
| 4,551,346 | 11/1985 | Kilroy | 426/602 |

FOREIGN PATENT DOCUMENTS

| 0009404 | 4/1980 | European Pat. Off. | 514/938 |
| 2057957 | 5/1971 | Fed. Rep. of Germany | 514/938 |
| 2101044 | 3/1972 | France | 514/938 |

OTHER PUBLICATIONS

Watanabe, "Proteinaceous Surfactants . . . ", J. Food Sci., vol. 46, 1981, pp. 1467–1469.
Watanabe, "Characterization of Foam . . . ", Agric. Biol. Chem., 46(6), 1587–1592, (1982).

Primary Examiner—Matthew A. Thexton
Assistant Examiner—Catherine S. Kilby
Attorney, Agent, or Firm—Flynn, Thiel, Boutell & Tanis

[57] ABSTRACT

A proteinaceous emulsifier can be obtained by reacting an amino acid ester with a hydrophilic protein in the presence of an endopeptidase to form decomposition products of the hydrophilic protein having a carboxyl end group joined to the amino group of the amino acid ester by amide linkage.

This proteinaceous emulsifier has a typical surfactant structure in which a hydrophobic portion consisting of the amino acid ester is attached to the rear end of a hydrophilic portion consisting of the protein, and is characterized by causing little irritation to the skin, exhibiting strong emulsifying power and possessing moisture retention properties. Thus, it is very suitable for use as an emulsifier in various cosmetics such as creams, milky lotions and the like.

13 Claims, 13 Drawing Sheets

PROTEINACEOUS EMULSIFIER, PROCESS FOR PREPARING SAME AND EMULSION TYPE COSMETIC COMPOSITIONS CONTAINING SAME

This application is a continuation of U.S. Ser. No. 751,775, filed June 25, 1985 now abandoned.

TECHNICAL FIELD

This invention relates to a proteinaceous emulsifier that causes little irritation to the skin or the like, exhibits strong emulsifying power and possesses moisture retention properties, a process for preparing the same, as well as emulsion type cosmetic compositions. such as creams and the like, containing the same.

BACKGROUND ART

Generally, emulsifiers are widely used in cosmetics, foods and the like. Emulsifiers used in cosmetics include anionic surfactants and nonionic surfactants. However, these emulsifiers are disadvantageous in that anionic surfactants are irritable to the skin and in that nonionic surfactants fail to exhibit sufficient emulsifying power and are more or less irritable to the skin. Moreover, since these emulsifiers cannot impart water retention properties to creams and the like, a moisture retentive agent such as glycerol or the like is added thereto according to the existing state of the art. However, this causes problems because the emulsion stability and/or feeling of the cosmetic may be altered.

Emulsifiers used in foods include sugar esters, fatty acid monoglycerides and the like. These emulsifiers and disadvantageous in that, since their emulsifying power is not so strong, they must be used in large amounts to achieve a sufficient degree of emulsification. Accordingly, it is desired to provide an emulsifier that causes little irritation to the skin, exhibits strong emulsifying power and possesses moisture retention properties.

DISCLOSURE OF THE INVENTION

In view of the above-described state of the art, an object of the present invention is to provide an emulsifier which causes little irritation to the skin, exhibits strong emulsifying power and possesses moisture retention properties, a process for preparing such an emulsifier, and emulsion type cosmetic compositions containing such an emulsifier.

According to one feature of the present invention, there is provided a proteinaceous emulsifier composed of decomposition product of a hydrophilic protein having a carboxyl end group joined to the amino group of an amino acid ester by amide linkage.

According to another feature of the present invention, there is provided a process for preparing proteinacous emulsifiers which comprises providing an amino acid ester and a hydrophilic protein and reacting the amino acid ester with the hydrophilic protein in the presence of an endopeptidase to form a proteinaceous emulsifier composed of decomposition products of the hydrophilic protein having a carboxyl end group joined to the amino group of the amino acid ester.

According to still another feature of the present invention, there is provided a process for preparing proteinaceous emulsifiers in which, where the aforesaid amino acid ester is represented by the general formula (I) given below, the amino acid ester is reacted with the hydrophilic protein to form a decomposition product of the hydrophilic protein having a carboxyl end group joined to the amino group of the amino acid ester, and the resulting reaction product is subjected to dialysis.

According to a further feature of the present invention, there is provided an emulsion type cosmetic composition containing, as the emulsifier, a proteinaceous emulsifier composed of a decomposition product of a hydrophilic protein having a carboxyl end group joined to the amino group of an amino acid ester by amide linkage.

BEST MODE FOR CARRYING OUT THE INVENTION

Figure 1:
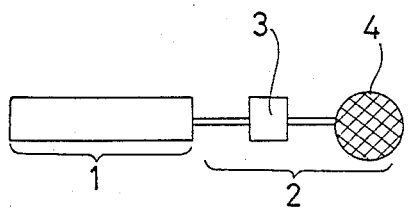
FIG. 1 is a schematic view illustrating a molecule of the proteinaceous emulsifier of the present invention.

The proteinaceous emulsifier of the present invention is composed of a decomposition product of a hydrophilic protein having a carboxyl end group joined to the amino group of an amino acid ester by amide linkage.

Specific examples of the amino acid ester used in the present invention include amino acid esters derived from alanine, glycine, tyrosine and tryptophan. They further include amino acid esters derived from amino acids having a side chain at the a-position such as valine, leucine, isoleucine, etc.; basic amino acids such as lysine, arginine, histidine, etc.; and dibasic amino acids such as aspartic acid, glutamic acid, etc. Among the above-enumerated amino acid esters, esters of basic amino acids are unstable and tend to become colored brown. Moreover, esters of dibasic amino acids may form practically unseparable by-products during the so-called aminolysis reaction (or enzymatic reaction) in which an amino acid ester is joined, by amide linkage, to the carboxyl end group of a decomposition product of a hydrophilic protein. Such by-products are undesirable because they may give off an offensive odor and degrade the stability of the proteinaceous emulsifier. The alcohols constituting the above-enumerated amino acid esters include alcohols having 2 to 22 carbon atoms, such as ethanol, propanol, butanol, heptanol, hexanol, octanol, decanol, dodecanol, myristyl alcohol, pentadecyl alcohol, cetyl alcohol, heptadecyl alcohol, stearyl alcohol, arachyl alcohol, behenyl alcohol and the like.

They also include unsaturated alcohols such as 2-pentenol-1, 11-dodecenol-1, oleyl alcohol and the like. In the case of unsaturated alcohols, the trans isomer is preferred to the cis isomer because the former exhibits a higher degree of reactivity in the enzymatic reaction (or aminolysis reaction) involving the grafting of a hydrophilic protein. They further include branched-chain alcohols such as isopropyl alcohol, isobutyl alcohol, tert-butyl alcohol and the like. In the case of branched-chain alcohols, the iso form of alcohols are preferred because alcohols having an unduly bulky configuration exhibit a low degree of reactivity in the enzymatic reaction (or aminolysis reaction).

In consideration of the above-described facts, preferred examples of the amino acid ester constituting the emulsifier of the present invention are amino acid esters represented by the formula

$$R_1CH(NH_2)COOR_2 \quad (1)$$

where $R_1$ is hydrogen, an alkyl group, an ω-hydroxyalkyl group, an aralkyl group or an ω-hydroxyaralkyl group and $R_2$ is a saturated hydrocarbon or unsaturated hydrocarbon radical having 2 to 22 carbon atoms.

Among amino acid esters represented by the above formula (1), amino acid esters in which the substituent group $R_1$ has a high degree of hydrophobicity are more preferred and these amino acid esters are represented by the formula

$$R_3CH(NH_2)COOR_2 \quad (2)$$

where $R_3$ is a methyl, isopropyl, n-butyl, isobutyl, sec-butyl, 1-hydroxyethyl, benzyl or p-hyroxybenzyl group and $R_2$ is as defined for formula (1).

Specific examples of amino acid esters represented by the above formula (2) include esters of alanine, valine, norleucine, leucine, isoleucine, threonine, phenylalanine and tyrosine.

Among amino acid esters represented by the above formula (2), it is preferable to use an amino acid ester whose alcohol residue has 14 to 22 carbon atoms. If an amino acid ester whose alcohol residue has less than 14 carbon atoms is used, the resulting proteinaceous emulsifier will have poor emulsifying power and unemulsified compositions containing it may give off a slightly offensive odor after prolonged storage at high temperature (e.g., at 45° C. for 6 months). On the other hand, if an amino acid ester whose alcohol residue has more than 22 carbon atoms is used, the amino acid ester will tend to have poor solubility and, therefore, exhibit a low degree of reactivity in the enzymatic reaction (or aminolysis reaction) with a hydrophilic protein. Accordingly, it is preferable to use an amino acid ester whose alcohol residue has 14 to 22 carbon atoms.

As is evident from Example 14 and Table 11 which will be given later, this tendency is marked especially where leucine is used as the amino acid. Accordingly, where leucine is used as a constituent of the emulsifier of the present invention, it may safely be said that the most preferred leucine esters are ones represented by

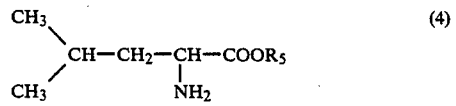

$$\begin{matrix} CH_3 \\ \phantom{CH_3}\diagdown \\ \phantom{CHCH}CH-CH_2-CH-COOR_5 \\ \phantom{CH_3}\diagup \phantom{CH-CH_2-}| \\ CH_3 \phantom{CH-CH_2-CH}NH_2 \end{matrix} \quad (4)$$

where $R_5$ is a saturated aliphatic hydrocarbon or unsaturated aliphatic hydrocarbon radical having 14 to 22 carbon atoms.

Furthermore, an investigation has been made as to the differences in emulsifying power based on the type of amino acid of the amino acid ester constituting the emulsifier of the present invention. Thus, as is evident from Example 23 and 24 and FIG. 12 which will be given later, the most preferred amino acid esters are alanine esters represented by

$$\begin{matrix} CH_3CHCOOR_4 \\ | \\ NH_2 \end{matrix} \quad (3)$$

where $R_4$ is a saturated aliphatic hydrocarbon or unsaturated aliphatic hydrocarbon radical having 2 to 22 carbon atoms.

Second to such alanine esters are esters composed of leucine and an alcohol having 14 to 22 carbon atoms, esters derived from isoleucine, and esters derived from tyrosine. Esters derived from glycine are slightly inferior in emulsifying power to the above-enumerated esters.

Although the amino acids constituting the above-enumerated esters include L-amino acids and D-amino acids, it is preferable to use an L-amino acid. If a D-amino acid is used, the yield of the resulting proteinaceous emulsifier will be reduced.

As the hydrophilic protein constituting the proteinaceous emulsifier of the present invention, gelatin is most preferred because of its hydrophilicity and safety, as well as its solubility in the reaction system, reaction efficiency and other characteristics desirable for the enzymatic reaction. In the second place, casein, sericin, soluble collagen and zein are preferable.

The above-described proteinaceous emulsifier can be prepared, for example, in the following manner. Specifically, an amino acid is first reacted with an alcohol to synthesize an amino acid ester to which decomposition products of a hydrophilic protein are to be joined.

In the synthesis of an amino acid ester, any of the well-known esterification reactions may be properly chosen and effected by using a strong acid (such as sulfuric acid or the like) or a Lewis acid (such as zinc oxide, activated alumina, tetraisopropyl titanate or the like) as the catalyst. However, more excellent results can be obtained by employing the following process which proceeds by way of p-toluenesulfonate of a free amino acid ester. That is, an amino acid is reacted with an alcohol in the presence of the p-toluenesulfonate, a Bronsted acid catalyst, to form the p-toluenesulfonate of an amino acid ester.

Since the esterification reaction is carried out in the presence of p-toluenesulfonic acid, the amino acid ester is not obtained in the free state, but in the form of an amino acid ester p-toluenesulfonate. In the practice of the present invention, this salt can also be used in the reaction with decomposition products of a hydrophilic protein and, therefore, can be a raw material for the preparation of the emulsifier of the present invention.

However, when reacted with a hydrophilic protein in the presence of an endopeptidase, this amino acid ester p-toluenesulfonate is poorly soluble in the solvent comprising a mixture of a buffer solution and acetone. Especially where the alcohol residue constituting the amino acid ester has 14 or more carbon atoms, it becomes more difficult to establish a homogeneous system as the chain is lengthened, and the yield of the resulting proteinaceous emulsifier is less than desirable. Moreover, the amino acid ester p-toluenesulfonate can hardly be freed of impurities such as unreacted amino acid, p-toluenesulfonic acid and the like, even though the product resulting from the esterification reaction is purified by recrystallizing it repeatedly from suitable solvents such as acetone and the like to remove unreacted impurities. Accordingly, if the amino acid ester p-toluenesulfonate is used as such, the degree of conversion into the desired proteinaceous emulsifier will be low, and what is more, the resulting proteinaceous emulsifier will be contaminated with appreciable amounts of impurities. Thus, in order to obtain a high pure proteinaceous emulsifier, it will be necessary to wash the product repeatedly with hot acetone or the like in the final step of the process. For these reasons, it is advantageous to subject the amino acid ester p-toluenesulfonate to an alkali treatment (under salting-out conditions, if desired) and use the resulting free amino acid ester in the reaction with a hydrophilic protein. As the alkaline medium, an aqueous solution of NaOH or KOH is preferably used. The alkali concentration is preferably in the range of 0.01N to 5N and more preferably in the range of 0.05N to 2N. It is also preferable to carry out the aforesaid alkali treatment under salting-out conditions, i.e., in the coexistence of a salt. The salts useful for salting-out purposes include alkali metal salts, ammonium salts and the like. Specific examples thereof include sodium chloride, potassium chloride, potassium carbonate, potassium phosphate, ammonium sulfate, sodium sulfate and the like. However, sodium chloride and potassium chloride are preferred. The salt concentration used for salting-out purposes is usually in the range of 0.5 to 25% and preferably in the range of 1 to 10%. While the aforesaid amino acid ester p-toluenesulfonate is a solid, the free amino acid ester thus obtained is in the form of an oil or a low-melting solid. Thus, during the succeeding reaction with a hydrophilic protein, the free amino acid ester is very easily soluble in the reaction solvent comprising, for example, a mixture of a buffer solution and acetone. Accordingly, the reaction can be carried out in a homogeneous system.

However, where an alanine ester represented by the above formula (3) is used as the amino acid ester, desirable results can be obtained by using the resulting alanine ester p-toluenesulfonate as such, i.e., without eliminating p-toluenesulfonic acid from the alanine ester p-toluenesulfonate. Specifically, alanine esters, though in the form of p-toluenesulfonates, exhibit excellent solubility. Thus, even if an alanine ester p-toluenesulfonate is used as such, any residues (such as unreacted alanine, p-toluenesulfonic acid and the like) remaining in the reaction system are effectively removed, as contrasted with the case in which other amino acid esters are used. Accordingly, the desired product can be obtained in a highly purified state.

It is to be understood that, in order to distinguish between free amino acid esters and their p-toluenesulfonates in the following description given in this specification, the term "free amino acid ester" exclusively denotes compounds represented by the above general formula (1), while the term "amino acid ester" is used in its broadest sense and comprehends both such compounds and their p-toluenesulfonates.

The amino acid ester obtained in the above-described manner is then reacted with a hydrophilic protein as described below in the presence of an endopeptidase as described below.

(Hydrophilic Proteins)

Casein, gelatin, sericin, soluble collagen, zein, serum albumin, lactalbumin and egg albumin may be used alone or in combination. Among these proteins, other proteins that sericin are commercially available reagents. Sericin can be obtained by extracting cut cocoons with hot water and freeze-drying the extract. It is most preferable to use gelatin because of its hydrophilicity, safety and other desirable properties, as well as its solubility in the reaction system, reaction efficiency and other characteristics desirable for the enzymatic reaction.

(Endopeptidases)

Endopeptidases have the effect of splitting protein at centrally located points of its molecule, and include serine proteases, thiol proteases, carboxyl proteases, metal proteases and other endopeptidases. Among them, thiol proteases are most preferably used. Useful thiol proteases include papain, ficin, cathepsin B, kiwi fruit protease, bromelain, chymopapain, cathepsin L, yeast proteinase B, cathepsin S and TZ-peptidase, which may be used alone or in combination.

When the amino acid ester is reacted with a hydrophilic protein in the presence of an endopeptidase, the hydrophilic protein is split at centrally located points by the action of the endopeptidase and, at the same time, the carboxyl end group of the resulting decomposition products thereof is joined to the amino group of the amino acid ester by amide linkage. Thus, there is obtained a proteinaceous emulsifier in accordance with the present invention.

If a free amino acid ester is used in the above-described reaction with a hydrophilic protein, the free amino acid ester can be uniformly dispersed in the solvent of the reaction system because of its desirable form (i.e., an oil or a low-melting solid). Accordingly, when a free amino acid ester is reacted with a hydrophilic protein in the presence of an endopeptidase, the reaction efficiency is so markedly improved that a highly pure proteinaceous emulsifier having excellent emulsification characteristics can be obtained in high yield.

One suitable method for after-treatment of the resulting enzymatic reaction product is dialysis. Specifically, after the endopeptidase remaining in the enzymatic reaction product is deactivated under acid conditions, the enzymetic reaction product is subjected to dialysis. The dialysis may be carried out by use of a hollow-fiber ultrafiltration membrane, especially contained in a cylindrical housing, to obtain desirable results. As the material of the hollow-fiber ultrafiltration membrane, there may be used cellulose acetate, cellulose, polyacrylonitrile, ethylene vinyl alcohol, polyvinyl alcohol, Cuprofan membrane (manufactured by Enka GmbH, West Germany) and the like. Preferably, cellulose, polyacrylonitrile or Cuprofan membrane is chosen.

In dialyzing and concentrating the enzymetic reaction product by use of such a hollow-fiber ultrafiltration membrane, the hollow-fiber ultrafiltration membrane is preferably kept at a temperature of 25° C. to 50° C. and more preferably at a temperature of 35° C. to 45° C.

By using such a hollow-fiber ultrafiltration device for purposes of dialysis and concentration, the enzymatic reaction product can be deodorized perfectly and, moreover, can be desalted and concentrated in a very short period of time.

Furthermore, since the water content has been reduced in the aforesaid concentration step, a subsequent drying step can also be carried out in an economical manner and in a short period of time. Thus, an odorless proteinaceous emulsifier can be obtained in a short period of time and in an economical manner, and further in high yield.

A schematic view illustrating a molecule of the emulsifier of the present invention is shown in FIG. 1. In this figure, reference numeral 1 designates a portion consisting of a decomposition product of a hydrophilic protein and reference numeral 2 designates a portion consisting of an amino acid ester which includes an amino acid moiety 3 and an alcohol residue moiety 4. In the proteinaceous emulsifier represented by the aforesaid schematic view, the portion 1 consisting of a decomposition product of a hydrophilic protein constitutes a hydrophilic portion and the portion 2 consisting of an amino acid ester constitutes a hydrophobic protein.

Since the hydrophilic portion 1 consists of a protein inherently having strong hydrophilicity and the hydrophobic portion 2 consists of a hydrophobic amino acid ester, this proteinaceous emulsifier has a typical surfactant structure (in which the front end of the hydrophobic portion 2 is attached to the rear end of the hydrophilic portion 1 and no extra hydrophobic portions are attached to intermediate points of the hydrophilic portion 1) and, therefore, exhibits strong emulsifying power. Moreover, since its emulsifying power is scarcely influenced by temperature due to the polymeric structure of the protein portion, this emulsifier does not show a reduction in emulsifying power, especially at low temperatures. Furthermore, since the aforesaid hydrophilic portion 1 has a relatively large molecular weight (of about 500 or more, and usually several thousands), the whole emulsifier also has a large molecular weight, thus causing little irritation to the skin or the like. In addition, this emulsifier possesses satisfactory moisture retention properties because the hydrophilic portion 1 consists of a protein inherently having moisture-retaining power. Accordingly, if this emulsifier is used in cosmetics, especially in creams, satisfactory water retention properties can be imparted thereto without using any conventional moisture-retaining agents such as polyhydric alcohols and the like.

Where the emulsifier of the present invention is prepared by using a free amino acid ester represented by formula (1) as the amino acid ester, the efficiency of the reaction between the free amino acid ester and the hydrophilic protein is significantly enhanced, so that the resulting proteinaceous emulsifier has markedly improved emulsification characteristics and hence strong emulsifying power.

Furthermore, where the enzymatic reaction product is subjected to dialysis as an after-treatment, the resulting proteinaceous emulsifier is odorless. Accordingly, even in absence of perfume, it can be used without giving any disagreeable feeling. Alternatively, it can be perfumed without spoiling the inherent odor of the perfume.

Thus, since the above-described proteinaceous emulsifier causes little irritation to the skin or the like, exhibits strong emulsifying power and possesses moisture retention properties, desirable effects are produced when it is used, for example, in cosmetics. When it is utilized as an emulsifer in foods, its strong emulsifying power makes it possible to reduce the amount of emulsifier used. Moreover, since most of the constituents of this emulsifier are derived from natural materials, no problem will arise even if it is ingested repeatedly.

Especially when the proteinaceous emulsifier is prepared by using an aliphatic alcohol ester of alanine represented by formula (3) as a raw material, it has excellent emulsifying power. Moreover, it has a pleasant odor as contrasted with proteinaceous emulsifiers derived from other amino acids. Furthermore, in the preparation thereof, such an aliphatic alcohol ester of alanine exhibits good solubility and other excellent properties. Thus the efficiency of the reaction between the ester and the hydrophilic protein is greatly enhanced to result in a marked improvement in yield.

As described above, the proteinaceous emulsifiers of the present invention have a typical surfactant structure in which a hydrophobic portion consisting of an amino acid ester is attached to the rear end of a hydrophilic portion consisting of a protein and are characterized by causing very little irritation to the skin, strong emulsifying power and moisture retention properties. Thus, when they are used in cosmetics, especially in creams and the like, water retention properties can be imparted thereto without using any polyhydric alcohol such as glycerol or the like, and the occurrence of skin diseases in persons having an irritable skin can be decreased markedly. Moreover, when they are utilized in foods, their strong emulsifying power makes it possible to reduce the amount of emulsifier used. Furthermore, according to the process of the present invention, an amino acid ester is reacted with a hydrophilic protein in the presence of an endopeptidase and, as soon as the hydrophilic protein is split, the amino acid ester is joined to the cut end of its decomposition product. Thus, an emulsifier having a typical surfactant structure in which a hydrophobic portion is attached to the rear end of a hydrophilic portion can be obtained with ease and in very high yield.

The emulsion type cosmetic compositions of the present invention contain a proteinaceous emulsifier as described above. The methods by which the emulsion type cosmetic compositions are made and the proteinaceous emulsifier is incorporated thereinto are not critical, and any of various conventional methods may be employed. Although various creams are typical of the emulsion type cosmetic compositions, it is to be understood that they include all types of cosmetics (such as milky lotions and the like) subjected to an emulsification procedure using an emulsifier.

In the emulsion type cosmetic compositions of the present invention, a proteinaceous emulsifier as described above may be used alone or in combination with any of conventional emulsifiers as described at the beginning of this specification.

As described above, the emulsion type cosmetic compositions of the present invention contain a proteinaceous emulsifier that has a typical surfactant structure in which a hydrophobic portion consisting of an amino acid ester is attached to the rear end of a hydrophilic portion consisting of a protein and is characterized by causing very little irritation to the skin, strong emulsifying power and moisture retention properties. More specifically, because of the moisture-retaining effect of the aforesaid emulsifier, these cosmetic compositions have satisfactory water retention properties without using any polyhydric alcohol such as glycerol or the like. Moreover, since the aforesaid emulsifier causes very little irritation to the skin, these cosmetic compositions give rise to no skin diseases even if a person having sensitive skin uses them continually. Furthermore, the strong emulsifying power of the aforesaid emulsifier makes it possible to reduce the amount of emulsifier used in the cosmetic compositions, which also contributes to the decrease in irritation to the skin.

The present invention is further illustrated by the following examples.

EXAMPLE 1 [PROTEINACEOUS EMULSIFIER 1]

An amino acid ester was prepared in the manner described below and then used in an enzymatic reaction.

(Synthesis of an Amino Acid Ester P-Toluenesulfonate)

Figure 2:
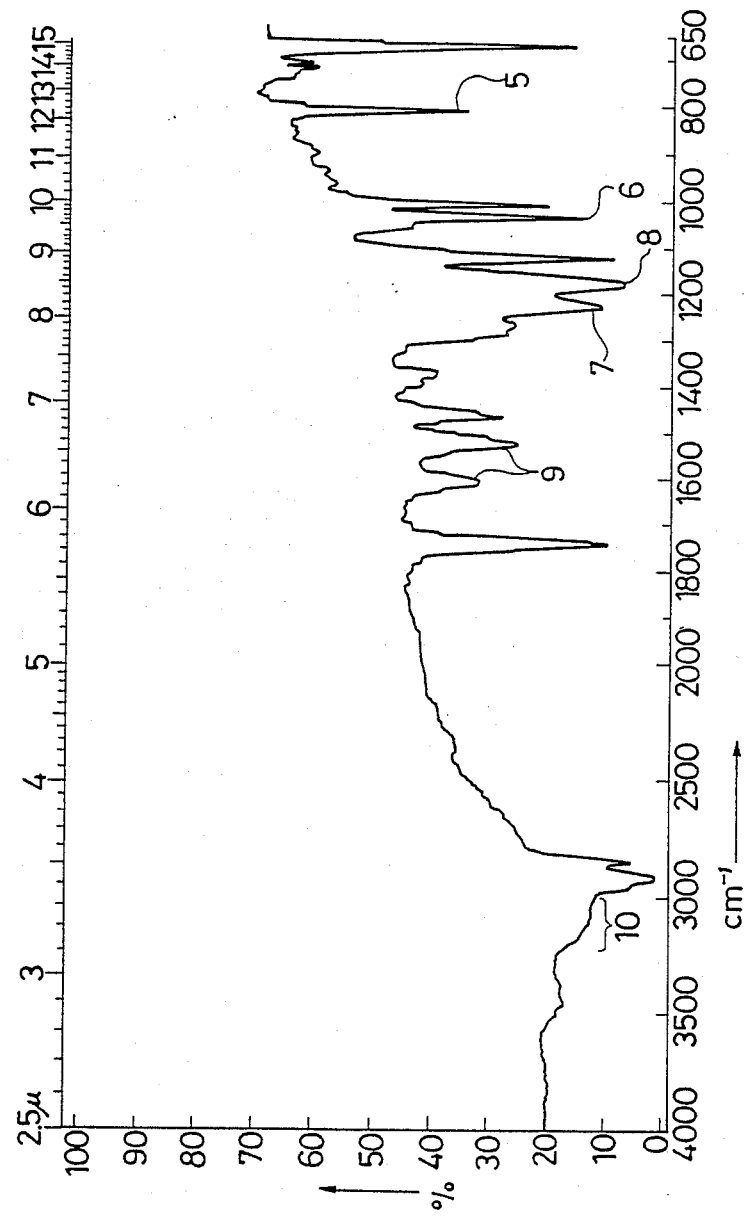
FIGS. 2 and 3 are infrared absorption spectra of amino acid ester p-toluenesulfonates used in the preparation of emulsifiers in accordance with the present invention.

0.05 mole of leucine was taken as an amino acid, 0.055 mole of p-toluenesulfonic acid hydrate was taken, and 0.075 mole of oleyl alcohol was taken as an alcohol. After 10 ml of benzene was added thereto as a solvent, these materials were stirred and mixed well. The resulting reaction mixture was heated at the reflux temperature of benzene to carry out the esterification reaction. In this case, water was formed with the progress of the esterification reaction and released in the form of an azeotropic mixture with benzene, which was continuously removed from the reaction system. Thus, the reaction was completed in about 5-10 hours. Then, the reaction mixture was concentrated under reduced pressure to remove the benzene used as solvent. After the addition of ether and petroleum ether, the precipitated crystals were collected by filtration. These crude crystals were recrystallized from acetone, ether, petroleum ether and the like. An infrared absorption spectrum of the leucine oleyl ester p-toluenesulfonate thus obtained is shown in FIG. 2. In this figure, the peak 5 indicates the absorption of light by a para-substituted phenyl group, the peaks 6 and 7 by the ester linkage, the peak 8 by sulfonic acid, and the peaks 9 and 10 by a primary amine salt.

(Enzymatic Reaction)

Figure 6:
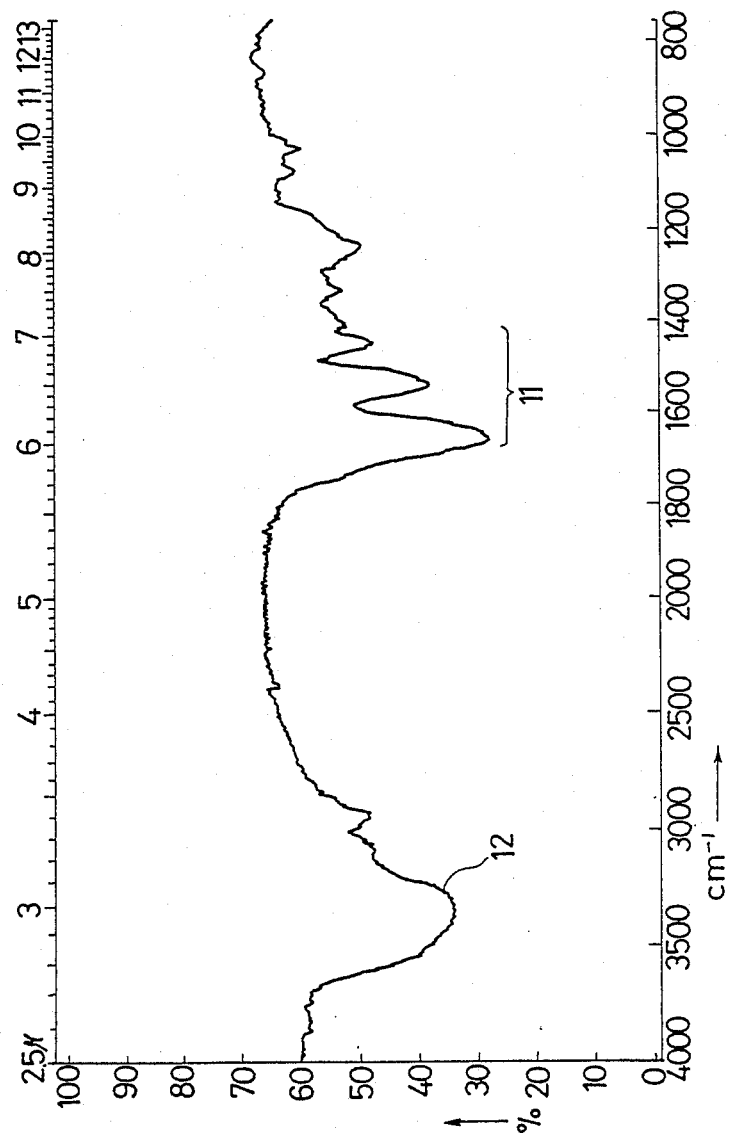
FIGS. 6 and 8 are infrared absorption spectra of proteinaceous emulsifiers in accordance with the present invention.

82 g of gelatin as a hydrophilic protein was dissolved in 200 g of a 1M carbonate buffer solution (pH 9.0). After the addition of 50 g of acetone, the resulting mixture was warmed in a water bath at 35° C. and homogenized by adequate stirring. Then, 30 g (i.e., 1 mole per 1,000 g of the gelatin) of leucine oleyl ester p-toluenesulfonate obtained in the above-described manner was added thereto and homogenized by adequate stirring. In this case, it is desirable from the viewpoint of reaction efficiency to use the amino acid ester (i.e., leucine oleyl ester) in an amount of 1 mole per 1,000 g of the hydrophilic protein (i.e., gelatin). Thereafter, 20 mg of 2-mercaptoethanol was added thereto, followed by 40 mg of crystalline papain (manufactured by Sigma Co.) as an endopeptidase. The resulting reaction mixture was stirred for 60 minutes, after which the reaction was stopped by bringing its pH to 2 with 1N hydrochloric acid. The reaction mixture was placed in a cellophane tube (or dialysis tube), dialyzed against running water for two days and nights, and then freeze-dried. The product was washed with hot acetone to remove any unreacted leucine oleyl ester and thereby obtain the desired proteinaceous emulsifier (hereinafter referred to as Proteinaceous Emulsifier 1). An infrared absorption spectrum of Proteinaceous Emulsifier 1 thus obtained is shown in FIG. 6. In this figure, the peak 11 indicate the absorption of light by protein and the peak 12 by hydrogen.

EXAMPLE 2 [PROTEINACEOUS EMULSIFIER2]

(Synthesis of an Amino Acid Ester P-Toluenesulfonate)

Glycine myrityl ester p-toluenesulfonate was prepared in substantially the same manner as in Example 1, except that glycine was used in place of leucine and myristyl alcohol was used in place of oleyl alcohol.

(Enzymatic Reaction)

Instead of 82 g of gelatin, 30 g of sericin was dissolved in 200 g of a 1M carbonate buffer solution. After the addition of 50 g of acetone, the resulting mixture was warmed on a water bath at 35° C. and homogenized by stirring. Then, 8.6 g (i.e., 1 mole per 1,000 g of the sericin) of glycine myristyl ester p-toluenesulfonate was added thereto and homogenized by stirring. Thereafter, an enzymatic reaction was carried out in the same manner as in Example 1 except that the amount of crystalline papain used was decreased to 20 mg. Thus, there was obtained Proteinaceous Emulsifier 2.

Figure 9:
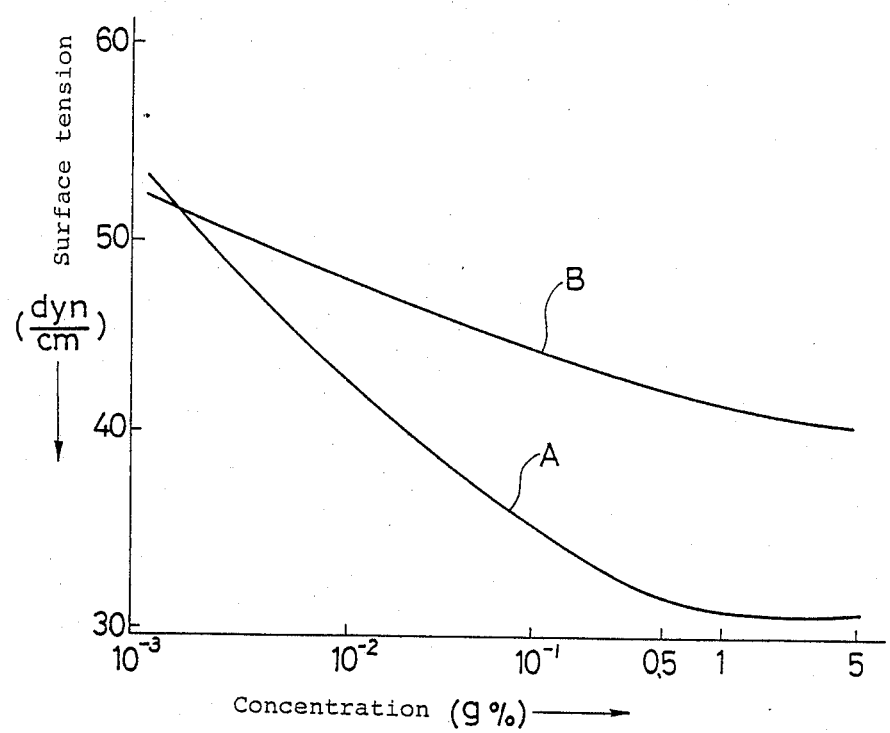
FIGS. 9 to 11 are surface tension diagrams of proteinaceous emulsifiers in accordance with the present invention.

Then, using Tween 80 as a control, the surface tension characteristics of Proteinaceous Emulsifier 1 obtained in the above-described Example 1 are shown in FIG. 9. In this figure, the concentration-surface tension curve of Proteinaceous Emulsifier 1 obtained in Example 1 is denoted by A and that of the control is denoted by B. By comparison of the curves A and B, it can be seen that Proteinaceous Emulsifier 1 obtained in Example 1 is markedly superior to Tween 80 in surface activity.

Then, the performance of the proteinaceous emulsifiers obtained in the above-described manner was evaluated by using them in a cosmetic composition and a food. In these cases, it was preferable from the viewpoint of effectiveness to use them in an amount of 1 to 2% by weight.

EXAMPLE 3 [SKIN CREAM]

Using the formulation given in Table 1 below, a skin cream was made according to conventional procedure. Specifically, Solution 1 was prepared by mixing the components 1, 2 and 3 given in Table 1 below at 80° C. until the mixture became homogeneous. On the other hand, Solution 2 was prepared by mixing the undermentioned components 4 to 6 at 80° C. until the mixture became homogeneous. Thereafter, while Solution 2 was being stirred in a homomixer, Solution 2 was added thereto and emulsified therein. The resulting emulsion was cooled, during which the undermentioned component 7 was added thereto at 70° C. When the temperature fell to 30° C., the stirring was discontinued to obtain a skin cream. The skin cream thus obtained was an O/W emulsion. On the other hand, another skin cream (Comparative Example 1) was made by using the undermentioned emulsifier (given in Comparative Example 1 of Table 1) in place of Proteinaceous Emulsifier 1.

TABLE 1

| | | (parts by weight) |
| --- | --- | --- |
| Component | Example 3 | Comparative Example 1 |
| 1. Cetyl alcohol | 10 | 10 |
| 2. Octyldodecyl myristate | 1.5 | 1.5 |
| 3. Liquid paraffin | 20.0 | 20.0 |
| 4. Emulsifier | Proteinaceous | Polyoxyethylene |

TABLE 1-continued

|  | | (parts by weight) |
|---|---|---|
| Component | Example 3 | Comparative Example 1 |
| | Emulsifier 1 of Example 1 2.0 | cetyl ether (10E.0) 2 Glycerol monostearate 1 |
| 5. Methylparaben | 0.3 | 0.3 |
| 6. Purifier water | 66.0 | 65.0 |
| 7. Perfume | 0.2 | 0.2 |

The results of performance tests of the resulting skin creams are shown in Table 2. As can be seen from Table 2, the skin cream of Example 3 was markedly superior to that of Comparative Example 1 in feeling, organoleptic effects and physiological effects on the skin.

TABLE 2

| Skin Cream Test item | Example 3 (persons/ persons) | Comparative Example 1 (persons/ persons) |
|---|---|---|
| (1) Appearance | | |
| Immediately after preparation | White, creamy | Same as left |
| After storage at 45° C. for 6 months | " | Same as left |
| After storage at 5° C. for 6 months | " | Same as left |
| (2) Smell | | |
| Immediately after preparation | Good | Same as left |
| After storage at 45° C. for 6 months | " | Same as left |
| After storage at 5° C. for 6 months | " | Same as left |
| (3) Feeling | | |
| Stickiness | 0/20 | 7/20 |
| Agglomeration | 0/20 | 5/20 |
| (4) Organoleptic effects | | |
| Finer texture | 16/20 | 8/20 |
| Better complexion | 15/20 | 7/20 |
| Tightened skin | 18/20 | 9/20 |
| (5) Physiological effects on skin | | |
| Improvement of dry skin | | |
| Effective | 16/20 | 8/20 |
| Slightly effective | 3/20 | 4/20 |
| Ineffective | 1/20 | 8/20 |
| Moisture-retaining effect | | |
| Effective | 15/20 | 8/20 |
| Slightly effective | 3/20 | 5/20 |
| Ineffective | 2/20 | 7/20 |
| Amelioration of keratinization | | |
| Effective | 17/20 | 7/20 |
| Slightly effective | 2/20 | 4/20 |
| Ineffective | 1/20 | 9/20 |

The results shown in Table 2 above were obtained according to the following test procedures.

(1) Appearance

The cream of Example 3 and the cream of Comparative Example 1 were stored at 45° C. or 5° C. for 6 months. Their appearance before and after storage was comparatively evaluated by 5 expert examiners.

(2) Smell

The cream of Example 3 and the cream of Comparative Example 1 was stored at 45° C. or 5° C. for 6 months. Their smell before and after storage was comparatively evaluated by 5 expert examiners.

(3) Feeling

Twenty female panelists were instructed to apply about 0.5 g of each of the two samples to the respective sides of the face. The occurrence of "stickiness" and/or "agglomeration" immediately after application was evaluated by the panelists themselves.

(4) Organoleptic effects

Twenty female panelists were instructed to apply about 0.5 g each of the two samples to the respective sides of the face. This application was made once a day and continued for 2 weeks. The state of the skin before and after testing was evaluated by the panelists themselves.

(5) Evaluation of the improvement of dry skin

Using 20 subjects of middle or advanced age having a dry skin on the legs, the effect of the creams was examined by applying them continually for 2 weeks. Specifically, about 1 g of a sample to be tested was applied once a day to a test area of the left leg of each subject. The state of the skin before and after testing was rated according to the following criteria. The right leg, to which no sample was applied was used as control.

Criteria for Rating the Dryness of the Skin

−: Normal.
±: Slightly dry, no desquamation.
+: Dry, slight desquamation.
++: Dry, moderate desquamation.
+++: Dry, marked desquamation.

The ratings of the test area before and after testing and the ratings of the control area were compared. The sample was judged to be "effective" when the dryness of the skin was improved by two or more steps (e.g., +→−or ++→±); "slightly effective" when the dryness was improved by one step; and "ineffective" when the dryness remained unchanged. No subjects showed an aggravation of the dryness of the skin.

(6) Evaluation of the moisture-retaining effect

Skin conductance was measured with a skin impedance meter (manufactured by IBS Co.). The moisture retention effect was evaluated by a short-term test in which the measurement was made 12 hours after a single application of a sample and by a continual-use test in which the measurement was made after a sample was applied once a day for 2 weeks. The tests were regarded as negative when the increase in skin conductance was less than 50%. The sample was judged to be "effective" when both the short-term test and the continual-use test were positive; "slightly effective" when only one of the tests was positive; and "ineffective" when both of the tests were negative.

(7) Evaluation of the amelioration of keratinization (or the improvement of resistance of scaling-off of horny layer)

After the above-described test for evaluating the improvement of dry skin, a piece of Scotch tape (Nichiban mending tape) was applied to the skin of the test area and then peeled off. The state of any horney layer adhering to the tape was closely examined with a scanning electron microscope. Thus, the amelioration of keratinization was evaluated by scoring the resistance of the skin to scaling-off of the horny layer according to the following criteria.

Criteria for Evaluating the Amelioration of Keratinization (or the Improvement of Resistance to Scaling-Off of Horny Layers)

Score 1: No scales are observed.
Score 2: Small-sized scales are scattered.
Score 3: Small- to medium-sized scales are abundant.
Score 4: Large-sized scales are abundant.

The score of the test area examined after continual application for 2 weeks was compared with that of the control area. The sample was judged to be "effective" when the difference between the two scores was 2 or more; "slightly effective" when the difference was 1; and "ineffective" when the difference was 0.

There were no cases in which the score of the test area was greater than that of the control area.

APPLICATION EXAMPLE 1 [ICE CREAM]

An ice cream was made by mixing raw materials in the proportion shown below and treating the mixture according to conventional procedure.

| Formulation | |
| --- | --- |
| Granulated sugar | 15 parts by weight |
| Milk powder | 10 parts by weight |
| Hydrogenated coconut oil | 5 parts by weight |
| Millet jelly powder (manufactured by Meiji Nyugyo K. K.) | 5 parts by weight |
| CMC | 0.2 parts by weight |
| Proteinaceous Emulsifier 2 (obtained in Example 2) | 0.3 parts by weight |
| Water | 64.5 parts by weight |

On the other hand, another ice cream (Comparative Example 2) was made by using the same amount of monostearin in place of Proteinaceous Emulsifier 2.

Then, the ice creams thus obtained were comparatively evaluated. As a result, when compared with the ice cream of Application Example 1, the ice cream of Comparative Example 2 had a poor gloss immediately after the manufacture thereof, and this poor gloss still persisted at the time of shipment and imparted thereto a quite unattractive appearance. In contrast, the ice cream of Application Example 1 had a good gloss immediately after the manufacture thereof and this good gloss lasted at least till the time of shipment. Moreover, the ice cream of Comparative Example 2 had the disadvantage that a sufficient overrun could not be achieved in the over-running step of the manufacturing process. However, such a disadvantage was not encountered in the ice cream of Application Example 1.

EXAMPLE 4 [PROTEINACEOUS EMULSIFIER 3]

Proteinaceous Emulsifier 3 was prepared in the same manner as described for Proteinaceous Emulsifier 2, except that lauryl alcohol was used in place of myristyl alcohol.

EXAMPLE 5 [PROTEINACEOUS EMULSIFIER 4]

Proteinaceous Emulsifier 4 was prepared in the same manner as described for Proteinaceous Emulsifier 2, except that octyl alcohol was used in place of myristyl alcohol.

Then, emulsion type cosmetic compositions were made using Proteinaceous Emulsifiers 1-4 prepared in the above-described manner. For this purpose, it has been found desirable from the viewpoint of effectiveness to use all of them in an amount of 1 to 3% by weight.

EXAMPLE 6 AND COMPARATIVE EXAMPLE 3 [MASSAGE CREAM]

In the formulations given in Table 3 below, Solution 1 was prepared by mixing the oily components 1 and 2 at 80° C. until the mixture became homogeneous. On the other hand, Solution 2 was prepared by mixing the water-soluble components 3, 4 and 5 at 80° C. until the mixture became homogeneous. Thereafter, while the aforesaid Solution 2 was being stirred in a homomixer, Solution 2 was added thereto and emulsified therein. The resulting emulsion was cooled, during which the below-mentioned component 6 was added thereto at 70° C. When the temperature fell to 30° C., the stirring was discontinued. Thus, there were obtained two massage creams of the O/W emulsion type.

TABLE 3

| | | (parts by weight) |
| --- | --- | --- |
| Component | Example 6 | Comparative Example 3 |
| 1. Liquid paraffin | 50 | 50 |
| 2. Cetyl alcohol | 5 | 5 |
| 3. Emulsifier | Proteinaceous Emulsifier 1 3 | Polyoxyethylene sorbitan mono-oleate (20E.0) 2.5 Sorbitan mono-oleate 2.5 |
| 4. Methylparaben | 0.2 | 0.2 |
| 5. Purifier water | 41.5 | 39.5 |
| 6. Perfume | 0.3 | 0.3 |

EXAMPLE 7 AND COMPARATIVE EXAMPLE 4 [SKIN MILK]

Using the formulations given in Table 4 below, two skin milks were made in the same manner as described in Example 6 except that Solution 1 was prepared from the oily components 1, 2 and 3 and Solution 2 was prepared from the water-soluble components 4, 5, 6 and 7.

TABLE 4

| | | (parts by weight) |
| --- | --- | --- |
| Component | Example 7 | Comparative Example 4 |
| 1. Cetyl alcohol | 6 | 6 |
| 2. Castor oil | 2 | 2 |
| 3. Liquid paraffin | 20 | 20 |
| 4. Emulsifier | Proteinaceous emulsifier 1 1.5 | Polyoxyethylene cetyl ether (5.5E.0) 2 Sorbitan sesquioleate 1 |
| 5. Propylene glycol | 5 | 5 |
| 6. Methylparaben | 0.5 | 0.2 |
| 7. Purifier water | 65.1 | 63.5 |
| 8. Perfume | 0.2 | 0.2 |

EXAMPLE 8 AND COMPARATIVE EXAMPLE 5 [SKIN MILK]

Using the formulations given in Table 5 below, two skin milks were made in the same manner as described in Example 6 except that Solution 1 was prepared from the oily components 1, 2 and 3 and Solution 2 was prepared from the water-soluble components 4, 5 and 6.

TABLE 5

| Component | Example 8 | Comparative Example 5 |
|---|---|---|
| 1. Cetyl alcohol | 5 | 5 |
| 2. Octyldodecyl myristate | 1.5 | 1.5 |
| 3. Liquid paraffin | 20.0 | 20.0 |
| 4. Emulsifier | Proteinaceous Emulsifier 1 2.0 | Polyoxyethylene cetyl ether (10E.0) 2 Glycerol monostearate 1 |
| 5. Methylparaben | 0.3 | 0.3 |
| 6. Purifier water | 71.0 | 70.0 |
| 7. Perfume | 0.2 | 0.2 |

(parts by weight)

EXAMPLE 9 AND COMPARATIVE EXAMPLE 6 [CLEANSING CREAM]

Using the formulations given in Table 6 below, two cleansing creams were made in the same manner as described in Example 6 except that Solution 1 was prepared from the oily components 1 and 2 and Solution 2 was prepared from the water-soluble components 3, 4 and 5.

TABLE 6

| Component | Example 9 | Comparative Example 6 |
|---|---|---|
| 1. Cetyl alcohol | 5 | 5 |
| 2. Liquid paraffin | 60 | 60 |
| 3. Emulsifier | Proteinaceous Emulsifier 2 3 | Polyoxyethylene monostearate (2.0E.0) 3 Sorbitan sesquioleate 2.5 |
| 4. Methylparaben | 0.2 | 0.2 |
| 5. Purifier water | 31.5 | 29.0 |
| 6. Perfume | 0.3 | 0.3 |

(parts by weight)

EXAMPLE 10 AND COMPARATIVE EXAMPLE 7 [CLEANSING MILK]

Using the formulations given in Table 7 below, two cleansing milks were made in the same manner as described in Example 6 except that Solution 1 was prepared from the oily components 1, 2 and 3 and Solution 2 was prepared from the water-soluble components 4, 5 and 6.

TABLE 7

| Component | Example 10 | Comparative Example 7 |
|---|---|---|
| 1. Liquid paraffin | 50 | 50 |

(parts by weight)

TABLE 7-continued

| Component | Example 10 | Comparative Example 7 |
|---|---|---|
| 2. Isocetyl myristate | 2 | 2 |
| 3. Xanthane gum | 1 | 1 |
| 4. Emulsifier | Proteinaceous Emulsifier 2 1 | Sorbitan sesquioleate 5 Polyoxyethylene monostearate (20E.0) 1.5 |
| 5. Methylparaben | 0.2 | 0.2 |
| 6. Purifier water | 45.5 | 43.5 |
| 7. Perfume | 0.3 | 0.3 |

(parts by weight)

EXAMPLE 11 AND COMPARATIVE EXAMPLE 8 [FOUNDATION CREAM]

Using the formulations given in Table 8 below, two foundation creams were made in the same manner as described in Example 6 except that Solution 1 was prepared from the oily components 1 and 2 and Solution 2 was prepared from the water-soluble components 3 to 9.

TABLE 8

| Component | Example 11 | Comparative Example 8 |
|---|---|---|
| 1. Liquid paraffin | 45 | 45 |
| 2. Ceresin | 5 | 5 |
| 3. Emulsifier | Proteinaceous Emulsifier 2 1.4 | Polyoxyethylene cetyl ether (5.5E.0) 2 Sorbitan sequioleate 1 |
| 4. Methylparaben | 0.3 | 0.3 |
| 5. Titanium oxide | 2.5 | 2.5 |
| 6. Kaolin | 1.25 | 1.25 |
| 7. Talc | 1.1 | 1.1 |
| 8. Yellow iron oxide | 0.4 | 0.4 |
| 9. Purified water | 43.05 | 41.45 |

(parts by weight)

EXAMPLE 12 [CLEANSING CREAM]

A cleansing cream was made in the same manner as described in Example 9 except that Proteinaceous Emulsifier 3 was used in place of Proteinaceous Emulsifier 2.

EXAMPLE 13 [CLEANSING CREAM]

A cleansing cream was made in the same manner as described in Example 9 except that Proteinaceous Emulsifier 4 was used in place of Proteinaceous Emulsifier 2.

The results of performance tests of the various creams obtained in the above-described examples and comparative examples are shown in Table 9. As can be seen from Table 9, the creams obtained in the examples were markedly superior to those obtained in the comparative examples, in feeling, organoleptic effects and physiological effects on the skin.

These tests were carried out according to the same procedures as described in Example 3.

TABLE 9

| | Example 6 | Comparative Example 3 | Example 7 | Comparative Example 4 | Example 8 | Comparative Example 5 | Example 9* | Comparative Example 6* | Example 10* | Comparative Example 7* | Example 11* | Comparative Example 8* | Example 12* | Example 13* |
|---|---|---|---|---|---|---|---|---|---|---|---|---|---|---|
| (1) Appearance | | | | | | | | | | | | | | |
| Immediately after preparation | White, creamy | Same as left | White, milky | Same as left | Same as left | Same as left | White creamy | Same as left | White, milky | Same as left | Skin-colored, creamy | Same as left | White, creamy | Same as left |
| After storage at 45° C. for 6 months | White, creamy | Same as left | White, milky | Same as left | Same as left | Same as left | White, creamy | Slight separation | White, milky | Same as left | Skin-colored, creamy | Same as left | White, creamy | Same as left |
| (2) Smell | | | | | | | | | | | | | | |
| Immediately after preparation | Good | Good | Good | Good | Good | Good | Good | Good | Good | Good | Good | Good | Good | Good |
| After storage at 45° C. for 6 months | " | " | " | " | " | " | " | " | " | " | " | " | Slightly offensive | Same as left |
| (3) Feeling | | | | | | | | | | | | | | |
| Stickiness (pers./pers.) | 0/20 | 7/20 | 0/20 | 6/20 | 0/20 | 7/20 | 0/20 | 6/20 | 0/20 | 5/20 | 0/20 | 7/20 | 0/20 | 0/20 |
| Agglomeration (pers./pers.) | 0/20 | 5/20 | 0/20 | 6/20 | 0/20 | 0/20 | 0/20 | 5/20 | 0/20 | 0/20 | 0/20 | 0/20 | 0/20 | 0/20 |
| (4) Organoleptic effects | | | | | | | | | | | | | | |
| Finer texture (pers./pers.) | 16/20 | 8/20 | 16/20 | 5/20 | 17/20 | 7/20 | 16/20 | 6/20 | 17/20 | 5/20 | 16/20 | 7/20 | 16/20 | 16/20 |
| Better complexion (pers./pers.) | 15/20 | 7/20 | 15/20 | 5/20 | 16/20 | 6/20 | 17/20 | 5/20 | 16/20 | 6/20 | 15/20 | 6/20 | 15/20 | 16/20 |
| Tightened skin (pers./pers.) | 18/20 | 9/20 | 18/20 | 7/20 | 17/20 | 8/20 | 17/20 | 8/20 | 17/20 | 7/20 | 18/20 | 7/20 | 17/20 | 17/20 |
| (5) Physiological effects on skin | | | | | | | | | | | | | | |
| Improvement of dry skin | | | | | | | | | | | | | | |
| Effective (pers./pers.) | 17/20 | 8/20 | 16/20 | 7/20 | 15/20 | 17/20 | 8/20 | 16/20 | 7/20 | 15/20 | 7/20 | | | |
| Slightly effective (pers./pers.) | 2/20 | 4/20 | 3/20 | 5/20 | 3/20 | 2/20 | 4/20 | 3/20 | 5/20 | 3/20 | 6/20 | | | |
| Ineffective (pers./pers.) | 1/20 | 8/20 | 1/20 | 8/20 | 2/20 | 1/20 | 8/20 | 1/20 | 8/20 | 2/20 | 7/20 | | | |
| Moisture-retaining effect | | | | | | | | | | | | | | |
| Effective (pers./pers.) | 16/20 | 8/20 | 15/20 | 7/20 | 16/20 | 16/20 | 8/20 | 15/20 | 7/20 | 16/20 | 5/20 | | | |
| Slightly effective (pers./pers.) | 3/20 | 5/20 | 3/20 | 3/20 | 3/20 | 3/20 | 5/20 | 3/20 | 3/20 | 3/20 | 6/20 | | | |
| Ineffective (pers./pers.) | 1/20 | 7/20 | 2/20 | 10/20 | 1/20 | 1/20 | 7/20 | 2/20 | 10/20 | 1/20 | 9/20 | | | |
| Amelioration of keratinization | | | | | | | | | | | | | | |
| Effective (pers./pers.) | 17/20 | 7/20 | 18/20 | 6/20 | 15/20 | 17/20 | 7/20 | 18/20 | 6/20 | 15/20 | 6/20 | | | |
| Slightly effective (pers./pers.) | 2/20 | 4/20 | 1/20 | 6/20 | 3/20 | 2/20 | 4/20 | 1/20 | 6/20 | 3/20 | 4/20 | | | |
| Ineffective (pers./pers.) | 1/20 | 9/20 | 1/20 | 8/20 | 2/20 | 1/20 | 9/20 | 1/20 | 8/20 | 2/20 | 10/20 | | | |

*Examples 9-13 and Comparative Examples 6-8 are concerned with cleansing creams, cleansing milks and foundation creams, which are intended to be washed away after application or have the effect of fixing other cosmetic to the face. Thus, their physiological effects on the skin were not tested because such effects are no more than secondary.

EXAMPLE 14 [PROTEINACEOUS EMULSIFIER 5]

A free amino acid ester was prepared in the manner described below and then used in an enzymatic reaction.

(Synthesis of Free Amino Acid Ester)

0.05 mole of leucine was used as an amino acid, 0.055 mole of p-toluenesulfonic acid hydrate was used, and 0.075 mole of myristyl alcohol was used as an alcohol. After 200 ml of benzene was added thereto as a solvent, these materials were stirred and mixed well. The resulting reaction mixture was heated at the reflux temperature of benzene to carry out the esterification reaction. In this case, water was formed with the progress of the esterification reaction and released in the form of an azeotropic mixture with benzene, which was continuously removed from the reaction system. Thus, the reaction was completed in about 5-10 hours. Then, the reaction mixture was concentrated under reduced pressure to remove the benzene used as solvent. After the addition of ether and petroleum ether, the precipitated crystals were collected by filtration. These crude crystals were recrystallized from acetone, ether, petroleum ether and the like.

The resulting leucine myristyl ester p-toluenesulfonate was dissolved again in 200 ml of benzene, and this solution was treated three times with 300—ml portions of 0.1N NaOH. Thereafter, the benzene layer was isolated and washed thoroughly with water. After washing with water, the benzene layer was isolated and dried overnight over anhydrous sodium sulfate. After drying, the benzene layer was filtered and the resulting benzene solution was evaporated to remove the solvent. Thus, purified free leucine myristyl ester was obtained in the form of an oily material.

Figure 4:
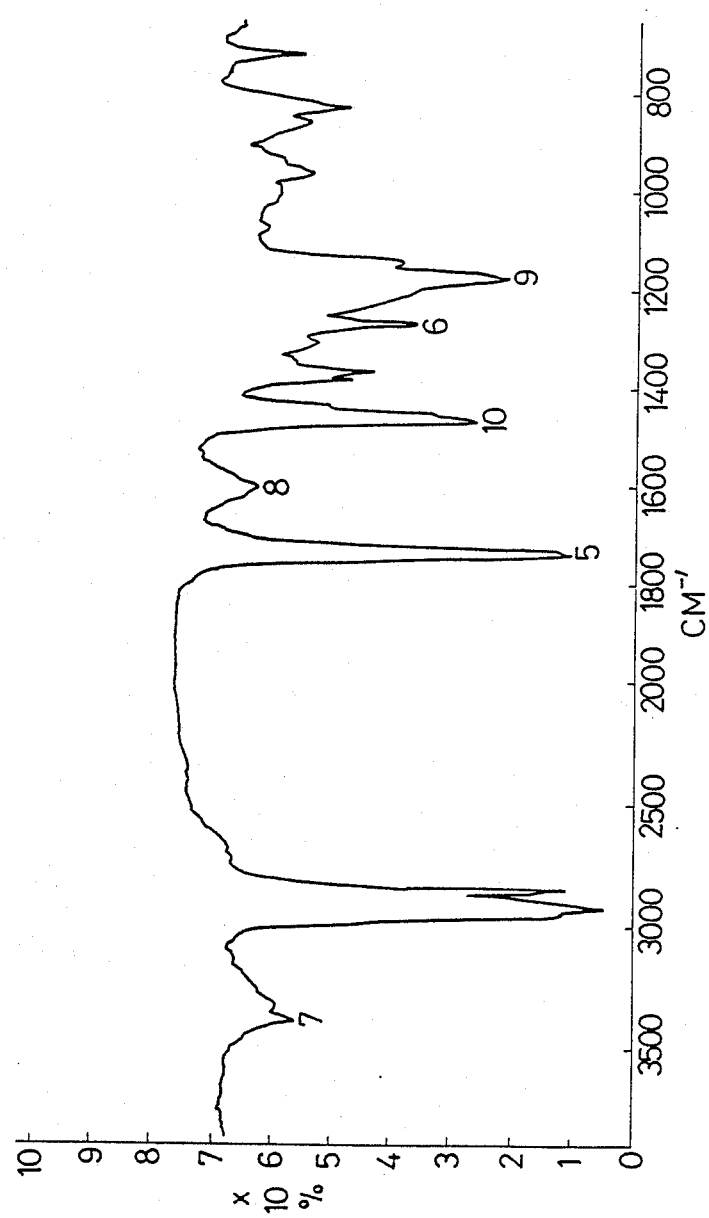
FIGS. 4 and 5 are infrared absorption spectra of free amino acid esters used in the preparation of emulsifiers in accordance with the present invention.

An infrared absorption spectrum of the leucine oleyl ester thus obtained is shown in FIG. 4. In this figure, the peaks 5 and 6 indicate the C=O stretching and C—O stretching vibrations originating from the ester linkage. The peaks 7, 8 and 9 indicate the NH stretching, NH deformation and C—N stretching vibrations, respectively, of a primary amine. The peak 10 indicates the CH deformation vibration.

(Enzymatic Reaction)

Figure 7:
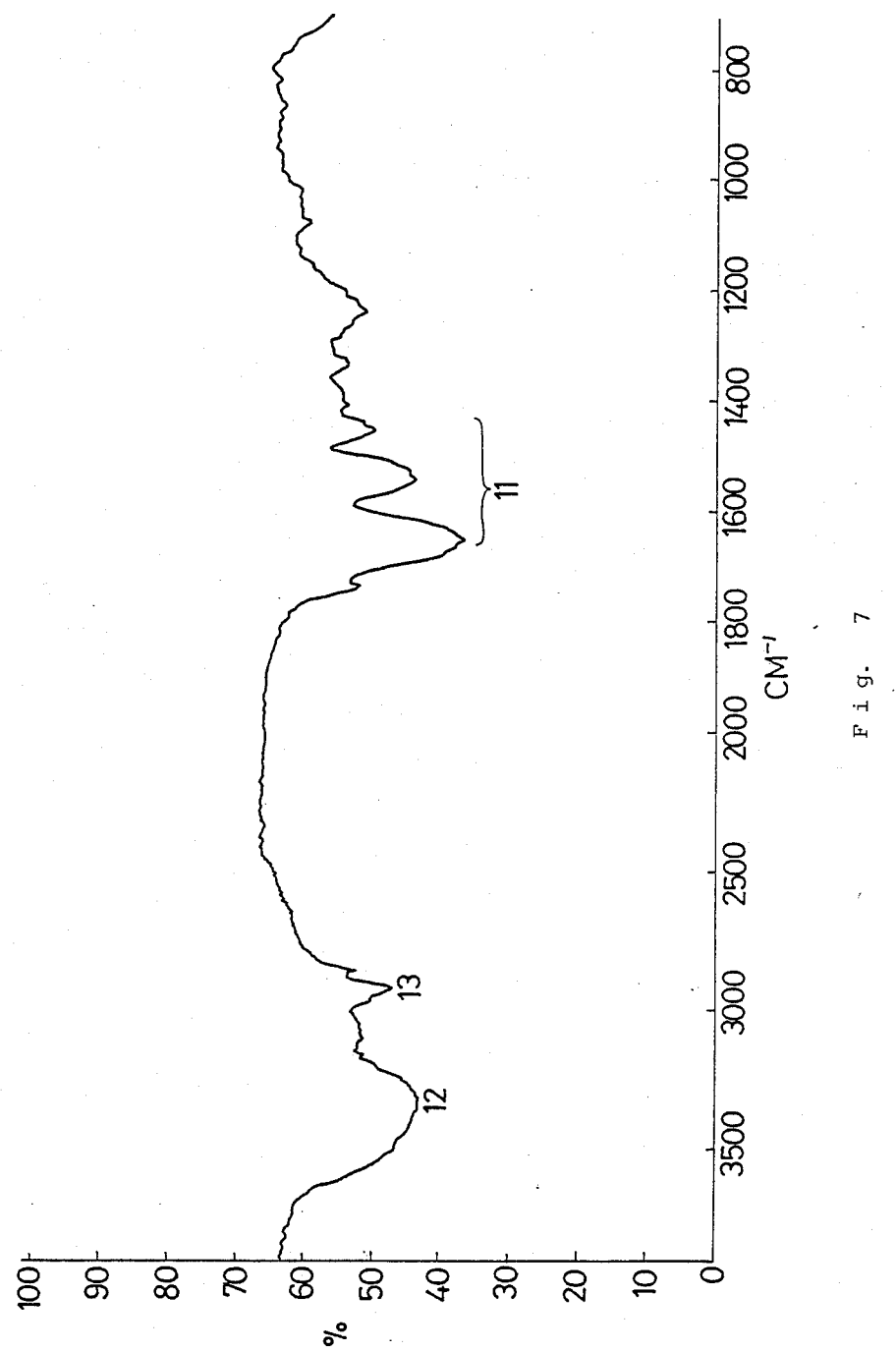

50 g of gelatin as a hydrophilic protein was dissolved in 200 ml of a 1M carbonate buffer solution (pH 9.0). After the addition of 50 g of acetone, the resulting mixture was warmed on a water bath at 37° C. and homogenized by adequate stirring. Then, 16.4 g (i.e., 1 mole per 1,000 g of the gelatin) of leucine myristyl ester obtained in the above-described manner was added thereto and homogenized by adequate stirring. In this case, it is desirable from the viewpoint of reaction efficiency to use the amino acid ester (i.e., leucine myristyl ester) in an amount of 1 mole per 1,000 g of the hydrophilic protein (i.e., gelatin). Thereafter, 438 mg of L-cysteine hydrochloride (manufactured by Wako Pure Chemicals Co., Ltd.) was added thereto, followed by 25 mg of papain (manufactured by Sigma Co.) as an endopeptidase. The resulting reaction mixture was stirred for 15 minutes, after which the reaction was stopped by bringing its pH to 2 with 2N hydrochloric acid. The reaction mixture was placed in a cellophane tube (or dialysis tube), dialyzed against running water for two days and nights, and then freeze-dried. The product was washed with hot acetone to remove any unreacted leucine myristyl ester and thereby obtain the desired proteinaceous emulsifier (hereinafter referred to as Proteinaceous Emulsifier 5). An infrared absorption spectrum of Proteinaceous Emulsifier 5 thus obtained is shown in FIG. 7. In this figure, the peak 11 indicates the absorption of light by protein and the peak 12 and 13 by hydrogen.

Other proteinaceous emulsifiers were prepared in the same manner as in the above example except that the p-toluenesulfonates of esters composed of leucine and each of the alcohols shown in Table 10 below and such esters in the free state were used in place of leucine myristyl ester p-toluenesulfonate and free leucine myristyl ester, respectively.

With regard to the cases in which the alcohol residue is lauryl, myristyl, cetyl, stearyl, arachyl and behenyl, the yield of the proteinaceous emulsifier obtained by reacting an amino acid ester p-toluenesulfonate with a hydrophilic protein and the yield of the proteinaceous emulsifier obtained by reacting a free amino acid ester with a hydrophilic protein were comparatively examined. The results thus obtained are shown in Table 10. It can be seen from this table that, at any chain length of the alcohol residue, the yield of the proteinaceous emulsifier obtained by reacting a free amino acid ester with a hydrophilic protein is significantly higher.

TABLE 10

| Ester | | Alcohol residue | | | | | |
|---|---|---|---|---|---|---|---|
| | | Lauryl $(C_{12})$ | Myristyl $(C_{14})$ | Cetyl $(C_{16})$ | Stearyl $(C_{18})$ | Arachyl $(C_{20})$ | Behenyl $(C_{22})$ |
| Leucine ester p-toluene-sulfonate | Amount used[*1] (g) | 9.43 | 9.99 | 10.55 | 11.12 | 11.68 | 12.24 |
| | Unreacted residue (g) | 1.15 | 2.68 | 4.15 | 6.22 | 6.74 | 6.98 |
| | Yield[*2] (mole %) | 87.8 | 73.7 | 60.7 | 44.1 | 42.3 | 43.0 |
| Free leucine ester | Amount used (g) | 5.99 | 6.55 | 7.1 | 7.67 | 8.23 | 8.79 |
| | Unreacted residue[*3] (g) | 0.55 | 1.3 | 2.01 | 3.13 | 3.73 | 4.02 |
| | Yield[*2] (mole %) | 89.5 | 82.15 | 74.4 | 62.8 | 58.4 | 57.8 |

[*1]The amount of reactant used per 20 g of the hydrophilic protein.
[*2]The yield (mole %) of the resulting proteinaceous emulsifier.
[*3]This residue was obtained in the form of a leucine ester hydrochloride.

The yields shown in Table 10 above were calculated as follows: In the final step, each proteinaceous emulsifier was washed three times with hot acetone. The acetone solutions obtained by filtration were combined and evaporated to remove the solvent. Then, the yield (mole %) was calculated from the amount of the unreacted leucine ester p-toluenesulfonate or leucine ester hydrochloride thus obtained. (The same shall apply hereinafter.)

$$\text{Yield (mole \%)} = \left[1 - \frac{\text{Amount of unreacted residue/molecular weight}}{\text{Amount of ester used/molecular weight}}\right] \times 100$$

The following tests for emulsifying power were carried out on four of the proteinaceous emulsifiers shown in Table 10 above, i.e., the proteinaceous emulsifiers obtained by reacting free leucine lauryl ester, free leucine myristyl ester, free leucine cetyl ester or free leucine stearyl ester with gelatin in the above example.

(Tests for Emulsifying Power)

25.0 parts by weight of liquid paraffin, 1.0 part by weight of a proteinaceous emulsifier and 74.0 parts by weight of water were mixed. The resulting mixture was homogenized at 9,000 rpm at 80° C. for 2 minutes and then cooled to room temperature. The emulsion so formed was centrifuged at 500 rpm for 25 minutes and the volume of the resulting cream layer was measured. The emulsifying power of the proteinaceous emulsifier was expressed as the volume of the cream layer divided by the total volume.

The results thus obtained are shown in Table 11 below.

TABLE 11

| Alcohol residue of free leucine ester constituting proteinaceous emulsifier | Emulsifying power |
|---|---|
| Lauryl ($C_{12}$) | 0.55 |
| Myristyl ($C_{14}$) | 0.80 |
| Cetyl ($C_{16}$) | 0.75 |
| Stearyl ($C_{18}$) | 0.65 |

As can be seen from the above table, the proteinaceous emulsifiers derived from leucine esters composed of leucine and an alcohol having 14 or more carbon atoms are much superior in emulsifying power to those in which the alcohol has 12 or less carbon atoms.

EXAMPLE 15 [PROTEINACEOUS EMULSIFIER 6]

A free amino acid ester was prepared in the manner described below and then used in an enzymatic reaction.

(Synthesis of a Free Amino Acid Ester)

0.05 mole of glycine was used as an amino acid, 0.055 mole of p-toluenesulfonic acid hydrate was used, and 0.075 mole of myristyl alcohol was used as an alcohol. After 200 ml of benzene was added thereto as a solvent, these materials were stirred and mixed well. The resulting reaction mixture was heated at the reflux temperature of benzene to carry out the esterification reaction. In this case, water was formed with the progress of the esterification reaction and released in the form of an azeotropic mixture with benzene, which was continuously removed from the reaction system. Thus, the reaction was completed in about 7 hours. Then, the reaction mixture was concentrated under reduced pressure to remove the benzene used as solvent. After the addition of ether and petroleum ether, the precipitated crystals were collected by filtration. These crude crystals were recrystallized from acetone, ether, petroleum ether and the like. The resulting glycine stearyl ester p-toluenesulfonate was dissolved again in 200 ml of benzene, and this solution was subjected to an alkali treatment under salting-out conditions by the addition of 300 ml of a 3% NaCl solution containing 0.1N NaOH. This alkali treatment was repeated three times. Thereafter, the benzene layer was isolated and washed thoroughly with a 3% NaCl solution. Thereafter, the benzene layer was treated in the same manner as in Example 14 to obtain purified free glycine stearyl ester.

(Enzymatic Reaction)

Instead of 50 g of gelatin, 30 g of zein was dissolved in 200 ml of a 1M carbonate buffer solution. After the addition of 50 ml of acetone, the reslting mixture was warmed on a water bath at 35° C. and homogenized by stirring. Then, 10.7 g (i.e., 1 mole per 1,000 g of the zein) of glycine stearyl ester which had previously been melted on a water bath at 50° C. was added thereto and homogenized by stirring. Thereafter, an enzymatic reaction was carried out in the same manner as in Example 14 except that the amount of crystalline papain used was decreased to 20 mg. Thus, there was obtained Proteinaceous Emulsifier 6.

Figure 10:
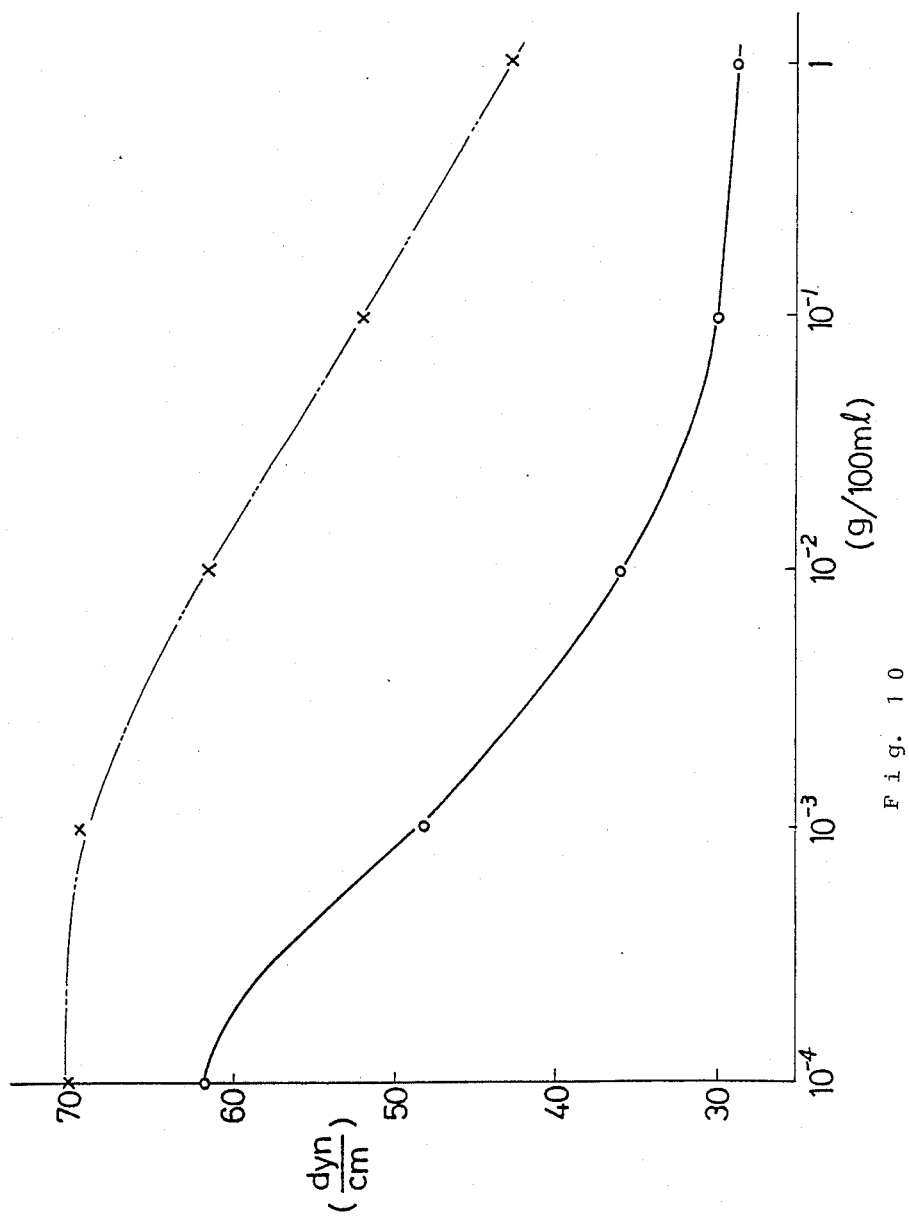

Then, using gelatin as a control, the surface tension characteristics of Proteinaceous Emulsifier 6 obtained in the above-described Example 14 are shown in FIG. 10. In this figure, the concentration-surface tension curve of Proteinaceous Emulsifier 6 obtained in Example 14 is denoted by A and that of the control is denoted by B. By comparison of the curves A and B, it can be seen that Proteinaceous Emulsifier 6 obtained in Example 14 is markedly superior to gelatin in surface activity.

EXAMPLE 6 [PROTEINACEOUS EMULSIFIER 7]

A free amino acid ester was prepared in the manner described below and then used in an enzymatic reaction.

(Synthesis of an Amino Acid Ester)

0.05 mole of leucine was taken as an amino acid, 0.055 mole of p-toluenesulfonic acid hydrate was taken, and 0.075 mole of myristyl alcohol was taken as an alcohol. After benzene was added thereto as a solvent, these materials were stirred and mixed well. The resulting reaction mixture was heated at the reflux temperature of benzene to carry out the esterification reaction. In this case, water was formed with the progress of the esterification reaction and released in the form of an azeotropic mixture with benzene, which was continuously removed from the reaction system. Thus, the reaction was completed in about 5–10 hours.

After being cooled to room temperature, the reaction mixture was washed three times with a 3% NaCl solution containing 0.3N NaOH. Thereafter, the benzene layer was isolated and washed thoroughly with a 3% NaCl solution until it became neutral. After being lightly washed with water, the benzene layer was isolated and dried overnight over anhydrous sodium sulfate. After drying, the benzene layer was filtered and the resulting benzene solution was evaporated to remove the solvent. Thus, purified free leucine myristyl ester was obtained in the form of an oily material.

(Enzymatic Reaction)

120 g of gelatin as a hydrophilic protein was dissolved in 480 ml of a 1M carbonate buffer solution (pH 9.0). After the addition of 120 ml of acetone, the resulting mixture was warmed on a water bath at 37° C. and homogenized by adequate stirring. Then, 39.3 g (i.e., 1 mole per 1,000 g of the gelatin) of leucine myristyl ester obtained in the above-described manner was added thereto and homogenized by stirring. In this case, it is desirable from the viewpoint of reaction efficiency to use the amino acid ester (i.e., leucine myristyl ester) in an amount of 1 mole per 1,000 g of the hydrophilic protein (i.e., gelatin). Thereafter, 1.05 g of L-cysteine hydrochloride (manufactured by Wako Pure Chemicals Co., Ltd.) was added thereto, followed by 60 mg of papain (manufactured by Sigma Co.) as an endopeptidase. The resulting reaction mixture was stirred for 15 minutes, after which the reaction was stopped by bringing its pH to 2 with 2N hydrochloric acid. The volume of the reaction mixture was about 1.5 liters. While being kept at about 40° C., this reaction mixture was fed to a hollow-fiber ultrafiltration device (using a Cuprofan mambrane and having an internal fiber diameter of 200µ, a membrane thickness of 11µ and an effective membrane area of 1.5 m$^2$) at a flow rate of about 10 ml/min. As the outer fluid, warm water at about 40° C. was fed at a flow rate of about 1 liter/min. After completion of the dialysis, the internal pressure of the same hollow-fiber ultrafiltration device was adjusted to about 2 kg/cm$^2$ and the dialyzed solution was concentrated under the same conditions as described above. Finally, about 700 ml of a concentrated solution was obtained.

This concentrated solution was dried with a spray dryer to obtain about 8.5 g of an odorless proteinaceous emulsifier (hereinafter referred to as Proteinaceous Emulsifier 7).

EXAMPLE 17 [PROTEINACEOUS EMULSIFIER 8]

A free amino acid ester was prepared in the manner described below and then used in an enzymatic reaction.

(Synthesis of a Free Amino Acid Ester)

0.05 mole of glycine was used as an amino acid, 0.055 mole of p-toluenesulfonic acid hydrate was used, and 0.075 mole of stearyl alcohol was used as an alcohol. After benzene was added thereto as a solvent, these materials were stirred and mixed well. The resulting reaction mixture was heated at the reflux temperature of benzene to carry out the esterification reaction. In this case, water was formed with the progress of the esterification reaction and released in the form of an azeotropic mixture with benzene, which is continuously removed from the reaction system. Thus, the reaction was completed in about 7 hours. After being cooled to room temperature, the reaction mixture was subjected to an alkali treatment under salting-out conditions by the addition of 300 ml of a 3% NaCl solution containing 0.5N NaOH. This alkali treatment was repeated three times. Thereafter, the benzene layer was isolated and washed thoroughly with a 3% NaCl solution. Thereafter, the benzene layer was treated in the same manner as in Example 16 to obtain purified free glycine stearyl ester in the form of an oily material.

(Enzymatic Reaction)

Instead of 120 g of gelatin, 70 g of zein was dissolved in 480 ml of a 1M carbonate buffer solution. After the addition of 120 ml of acetone, the resulting mixture was warmed on a water bath at 35° C. and homogenized by stirring. Then, 19.0 g (i.e., 1 mole per 1,000 g of the zein) of glycine stearyl ester which had previously been melted on a water bath at 50° C. was added thereto and homogenized by stirring. Thereafter, 1.05 g of L-cysteine hydrochloride (manufactured by Wako Pure Chemicals Co., Ltd.) was added thereto, followed by 45 mg of papain (manufactured by Sigma Co.) as an endopeptidase. The resulting reaction mixture was stirred for 15 minutes, after which the reaction was stopped by bringing its pH to 2 with 2N hydrochloric acid. The volume of the reaction mixture was about 1.5 liters. While being kept at about 40° C., this reaction mixture was fed to a hollow-fiber ultrafiltration device (using a cellulose membrane and having an internal fiber diameter of 200µ, a membrane thickness of 11µ and an effective membrane area of 2.4 m$^2$) at a flow rate of about 10 ml/min. As the outer fluid, warm water at about 40° C. was fed at a flow rate of about 1 liter/min. After completion of the dialysis, the internal pressure of the same hollow-fiber ultrafiltration device was adjusted to about 2 kg/cm$^2$ and the dialyzed solution was concentrated under the same conditions as described above. Finally, about 600 ml of a concentration solution was obtained.

This concentrated solution was dried with a spray dryer to obtain about 63 g of an odorless proteinaceous emulsifier (hereinafter referred to as Proteinaceous Emulsifier 8).

In Examples 16 and 17, the efficiency of the dialysis process using a hollow-fiber ultrafiltration device was comparatively evaluated by measuring the conductivity of the reaction mixture with a desk type digital conductivity meter (Model AO-6; manufactured by Electrochemical Instrument Co., Ltd.). The results thus obtained are shown in Table 12.

TABLE 12

|  |  | Conductivity |
| --- | --- | --- |
| Undialyzed reaction mixture | Example 16 | 4.3 mΩ |
|  | Example 17 | 4.8 mΩ |
| Dialyzed reaction mixture | Example 16 | 0.22 mΩ |
|  | Example 17 | 0.25 mΩ |
| Tap water |  | 0.19 mΩ |

As can be seen from Table 12, the conductivity of the reaction mixture having undergone a single dialysis is almost equal to that of tap water used as the outer fluid, indicating that a satisfactory dialysis efficiency was achieved.

As demonstrated above, when the reaction product is deodorized by a dialysis and concentration process using a hollow-fiber ultrafiltration membrane, a proteinaceous emulsifier characterized by causing little irritation to the skin or the like exhibiting strong emulsifying power and possessing moisture retention properties can be obtained in a perfectly deodorized state. Moreover, this can be accomplished in a short period of time and in an economical manner, and further, in high yield.

EXAMPLE 18 [PROTEINACEOUS EMULSIFIER 9]

An ester of alanine was prepared in the manner described below and then used in an enzymatic reaction.

(Synthesis of an L-alanine ester p-toluenesulfonate)

Figure 3:
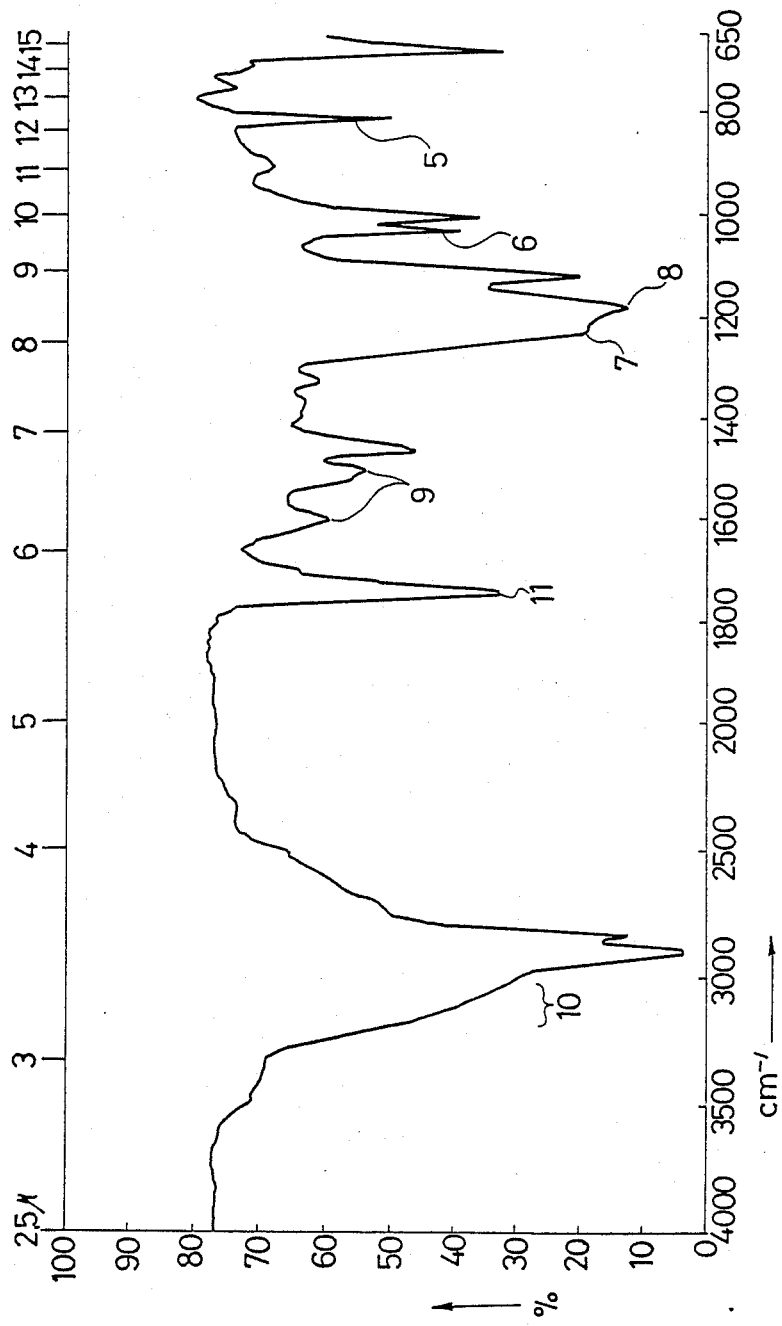

4.46 g (0.05 mole) of L-alanine was used, 11.4 g (0.06 mole) of p-toluenesulfonic acid hydrate was used, and 11.79 g (0.055 mole) of myristyl alcohol was used as an alcohol. After 200 ml of benzene was added thereto as a solvent, these materials were stirred and mixed well. The resulting mixture was heated at the reflux temperature of benzene to carry out the esterification reaction. In this case, water was formed with the progress of the esterification reaction and released in the form of an azeotropic mixture with benzene, which was continuously removed from the reaction system. Thus, the reaction was completed in about 7-15 hours. Then, the reaction mixture was concentrated under reduced pressure to remove the benzene used as solvent. After the addition of ether and petroleum ether, the precipitated crystals were collected by filtration. These crude crystals were recrystallized from acetone, ether, petroleum ether and the like to obtain 21.74 g (95% yield) of L-alanine myristyl ester p-toluenesulfonate. An infrared absorption spectrum of the L-alanine myristyl ester p-toluenesulfonate thus obtained is shown in FIG. 3. In this figure, the peak 5 indicates the absorption of light by a parasubstituted phenyl group, the peaks 6 and 7 by the ester linkage, the peak 8 by sulfonic acid, the peaks 9 and 10 by a primary amine salt, and the peak 11 by the C=O stretching vibration originating from the ester linkage.

(Enzymatic Reaction)

80 g of gelatin as a hydrophilic protein was dissolved in 200 g of a 1M carbonate buffer solution (pH 9.0). After the addition of 50 g of acetone, the resulting mixture was warmed on a water bath at 37° C. and homogenized by adequate stirring. Then, 37 g (i.e., 1 mole per 1,000 g of the gelatin) of L-alanine myristyl ester p-toluenesulfonate obtained in the above-described manner was added thereto and homogenized by adequate stirring. In this case, it is desirable from the viewpoint of reaction efficiency to use the amino acid ester (i.e., L-alanine myristyl ester) in an amount of 1 mole per 1,000 g of the hydrophilic protein (i.e., gelatin). Thereafter, 20 mg of 2-mercaptoethanol was added, followed by 40 mg of crystalline papain (manufactured by Sigma Co.) as an endopeptidase were added thereto. The resulting reaction mixture was stirred for 15 minutes, after which the reaction was stopped by bringing its pH to 2 with 2N hydrochloric acid. The reaction mixture was placed in a cellophane tube (or dialysis tubes), dialyzed against running water for two days and nights, and then freeze-dried. The product is washed with hot acetone to remove any unreacted L-alanine myristyl ester and thereby obtain 83 g of the desired proteinaceous emulsifier (hereinafter referred to as Proteinaceous Emulsifier 9).

EXAMPLE 19 [PROTEINACEOUS EMULSIFIER 10]

A free L-alanine ester was prepared in the manner described below and then used in an enzymatic reaction.

(Synthesis of a Free L-Alanine Ester)

Figure 5:
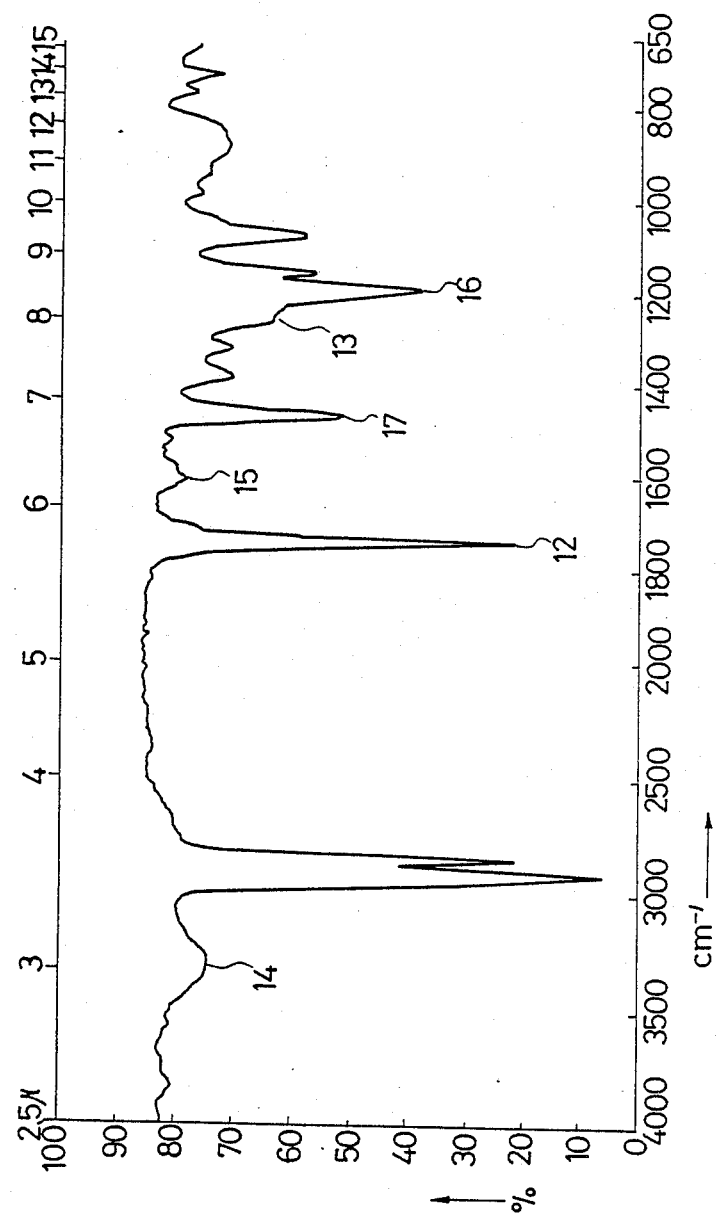

L-Alanine cetyl ester p-toluenesulfonate was synthesized in the same manner as described in Example 18 for the synthesis of an L-alanine alkyl ester p-toluenesulfonate, except that 13.3 g (0.055 mole) of cetyl alcohol was used in place of myristyl alcohol. The resulting L-alanine cetyl ester p-toluenesulfonate was dissolved again in 200 ml of benzene, and this solution was treated three times with 300-ml portions of 0.1N NaOH. Thereafter, the benzene layer was isolated and washed thoroughly with water. After washing with water, the benzene layer was isolated and dried overnight over anhydrous sodium sulfate. After drying, the benzene layer was filtered and the resulting benzene solution was evaporated to remove the solvent. Thus, there was obtained 14.86 g (94.8% yield) of purified free L-alanine cetyl ester in the form of an oily material. An infrared absorption spectrum of the free L-alanine cetyl ester thus obtained is shown in FIG. 5. In this figure, the peaks 12 and 13 indicate the C=O stretching and C—O stretching vibrations originating from the ester linkage. The peaks 14, 15 and 16 indicate the NH stretching, NH deformation and C—N stretching vibrations, respectively, of a primary amine. The peak 17 indicates the CH deformation vibration.

(Enzymatic Reaction)

Figure 8:
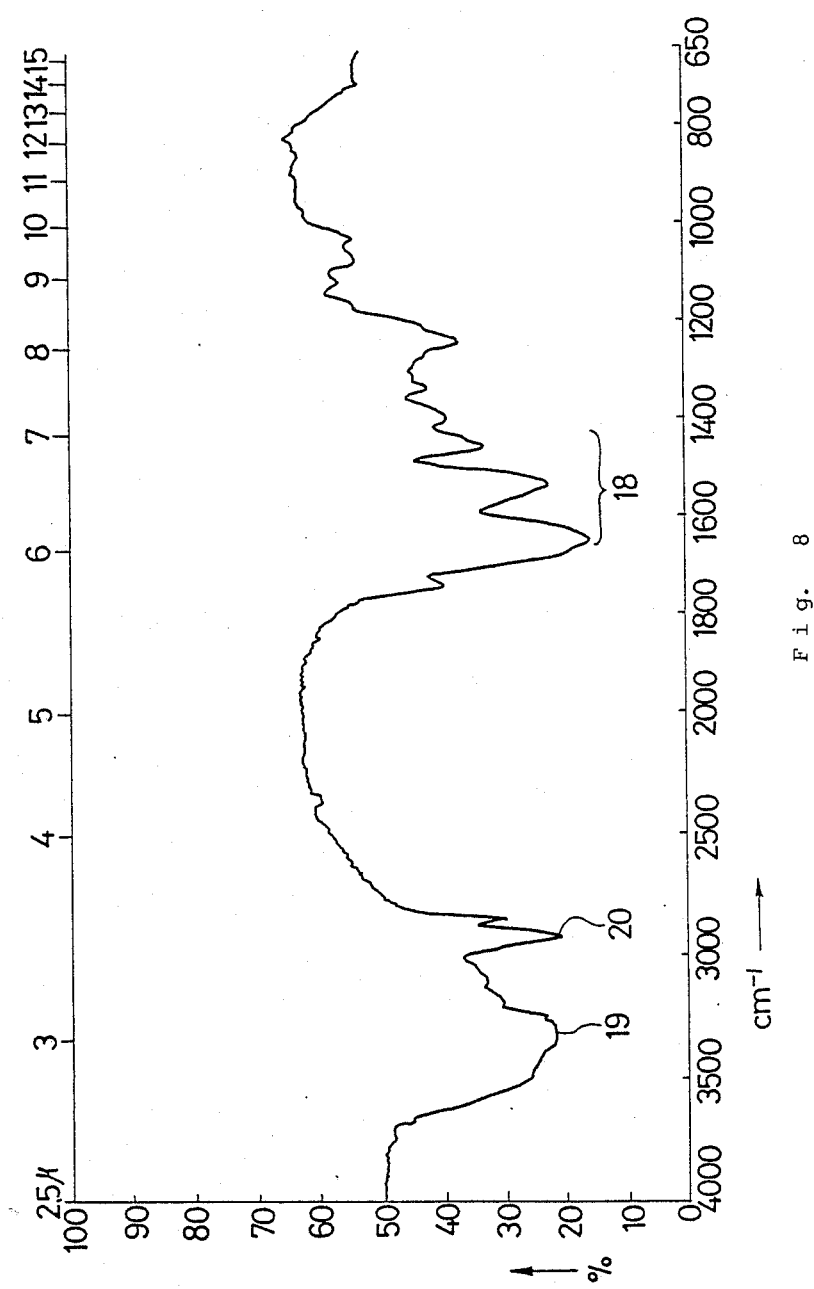

50 g of gelatin as a hydrophilic protein was dissolved in 200 ml of a 1M carbonate buffer solution (pH 9.0). After the addition of 50 ml of acetone, the resulting mixture was warmed on a water bath at 37° C. and homogenized by adequate stirring. Then, 15.7 g (i.e., 1 mole per 1,000 g of the gelatin) of L-alanine cetyl ester obtained in the above-described manner was added thereto and homogenized by adequate stirring. In this case, it is desirable from the viewpoint of reaction efficiency to use the amino acid ester (i.e., L-alanine cetyl ester) in an amount of 1 mole per 1,000 g of the hydrophilic protein (i.e., gelatin). Thereafter, 438 mg of L-cysteine hydrochloride (manufactured by Wako Pure Chemicals Co., Ltd.) was added thereto, followed by 25 mg of papain (manufactured by Sigma Co.) as an endopeptidase. The resulting reaction mixture was stirred for 15 minutes, after which the reaction was stopped by bringing its pH to 2 with 2N hydrochloric acid. The reaction mixture was placed in a cellophane tube (or dialysis tube), dialyzed against running water for two days and nights, and then freeze-dried. The product was washed with hot acetone to remove any unreacted leucine myristyl ester and thereby obtain 48.9 g of the desired proteinaceous emulsifier (hereinafter referred to as Proteinaceous Emulsifier 10). An infrared absorption spectrum of Proteinaceous Emulsifier 5 thus obtained is shown in FIG. 8. In this figure, the peak 18 indicates the absorption of light by protein and the peak 19 by hydrogen.

EXAMPLE 20 [(PROTEINACEOUS EMULSIFIER 11]

Proteinaceous Emulsifier 11 was prepared in the same manner as in Example 19 except that a free L-alanine ester was synthesized according to the following procedure.

(Synthesis of a Free L-Alanine Ester)

4.46 g (0.05 mole) of L-alanine was taken, and 13.3 g (0.055 mole) of cetyl alcohol was taken as an alcohol. After 200 ml of benzene was added thereto as a solvent, these materials were stirred and mixed. After the addition of 4.9 g (0.05 mole) of sulfuric acid as an acid catalyst, the resulting reaction mixture was heated under reflux. In this case, water was formed with the progress of the esterification reaction and released in the form of an azeotropic mixture with benzene, which was continuously removed from the reaction system. Thus, the reaction was completed in about 7 hours (at an internal temperature of 80.5° C.). After being cooled to room temperature, the reaction mixture was poured into a separating funnel and treated with 300 ml of a mixture of 0.2N NaOH and 6% NaCl solutions. This treatment was repeated three times. Thereafter, the benzene layer was isolated and washed thoroughly with water. After washing with water, the benzene layer was isolated and dried overnight over anhydrous sodium sulfate. Thereafter, the benzene layer was filtered and the resulting benzene solution was evaporated to remove the solvent. Thus, there was obtained 13.5 g (86.1% yield) of purified L-alanine cetyl ester in the form of an oily material.

EXAMPLE 21 [PROTEINACEOUS EMULSIFIER 12]

A free L-alanine ester was prepared in the manner described below and then used in an enzymatic reaction.

(Synthesis of a Free L-Alanine Ester)

L-Alanine stearyl ester p-toluenesulfonate was synthesized in the same manner as described in Example 18 for the synthesis of an L-alanine ester p-toluenesulfonate, except that 11.4 g (0.06 mole) of stearyl alcohol was used in place of myristyl alcohol. The resulting L-alanine stearyl ester p-toluenesulfonate was dissolved again in 200 ml of benzene, and this solution was treated three times with 300-ml portions of 0.4N NaOH. Thereafter, the benzene layer was isolated and washed thoroughly with water. After washing with water, the benzene layer was isolated and dried overnight over anhydrous sodium sulfate. After drying, the benzene layer was filtered and the resulting benzene solution was evaporated to remove the solvent. Thus, there was obtained 16.15 g (94.4% yield) of purified free L-alanine stearyl ester in the form of an oily material.

(Enzymatic Reaction)

120 ml of acetone was added to 480 ml of purified water and the resulting mixture was kept at 37° C. with stirring. 120 g of gelatin as a hydrophilic protein was added thereto. Then, 41 g (i.e., 1 mole per 1,000 g of the gelatin) of L-alanine stearyl ester obtained in the above-described manner was added thereto and homogenized by adequate stirring. The resulting reaction mixture was adjusted to pH 9.0 with 1N $Na_2CO_3$. On the other hand, an enzyme solution was prepared by adding 1.05 g of L-cysteine hydrochloride monohydrate and 62.5 mg of papain (manufactured by Sigma Co.) to 5 ml of purified water and preincubating this mixture at 37° C. for an hour with stirring. After the addition of this enzyme solution, the aforesaid reaction mixture was stirred at 37° C. for 20 minutes. Then, the reaction was stopped by bringing the pH to 2.0 with 2N hydrochloric acid. The total volume of the reaction mixture was about 1.5 liters. While being kept at about 40° C., this reaction mixture was fed to a hollow-fiber ultrafiltration device (using a Cuprofan membrane and having an internal fiber diameter of 200$\mu$, a membrane thickness of 11$\mu$ and an effective membrane area of 1.5 $m^2$) at a flow rate of about 10 ml/min. As the outer fluid, warm water at about 40° C. was fed at a flow rate of about 1 liter/min. After completion of the dialysis, the internal pressure of the same hollow-fiber ultrafiltration device was adjusted to about 2 kg/$cm^2$ and the dialyzed solution was concentrated under the same conditions as described above. Finally, about 800 ml of a concentrated solution was obtained. This concentrated solution was dried with a spray drier to obtain about 123 g of an odorless proteinaceous emulsifier (hereinafter referred to as Proteinaceous Emulsifier 12).

EXAMPLE 22 [PROTEINACEOUS EMULSIFIER 13]

Proteinaceous Emulsifier 13 was prepared by using L-leucine in place of L-alanine. Specifically, L-leucine myristyl ester p-toluenesulfonate was synthesized in the same manner as described in Example 18 for the synthesis of an L-alanine ester p-toluenesulfonate, except that L-leucine was used in place of L-alanine. The resulting p-toluenesulfonate was dissolved in 200 ml of benzene, and this solution was treated three times with 300-ml portions of 0.1N NaOH. Thereafter, the benzene layer was isolated and washed thoroughly with water. After washing with water, the benzene layer was isolated and dried overnight over anhydrous sodium sulfate. After drying, the benzene layer was filtered and the resulting benzene solution was evaporated to remove the solvent. Thus, purified L-leucine myristyl ester was obtained in the form of an oily material. Using this ester, an enzymatic reaction was carried out in the same manner as in Example 18 to obtain Proteinaceous Emulsifier 13.

Figure 11:
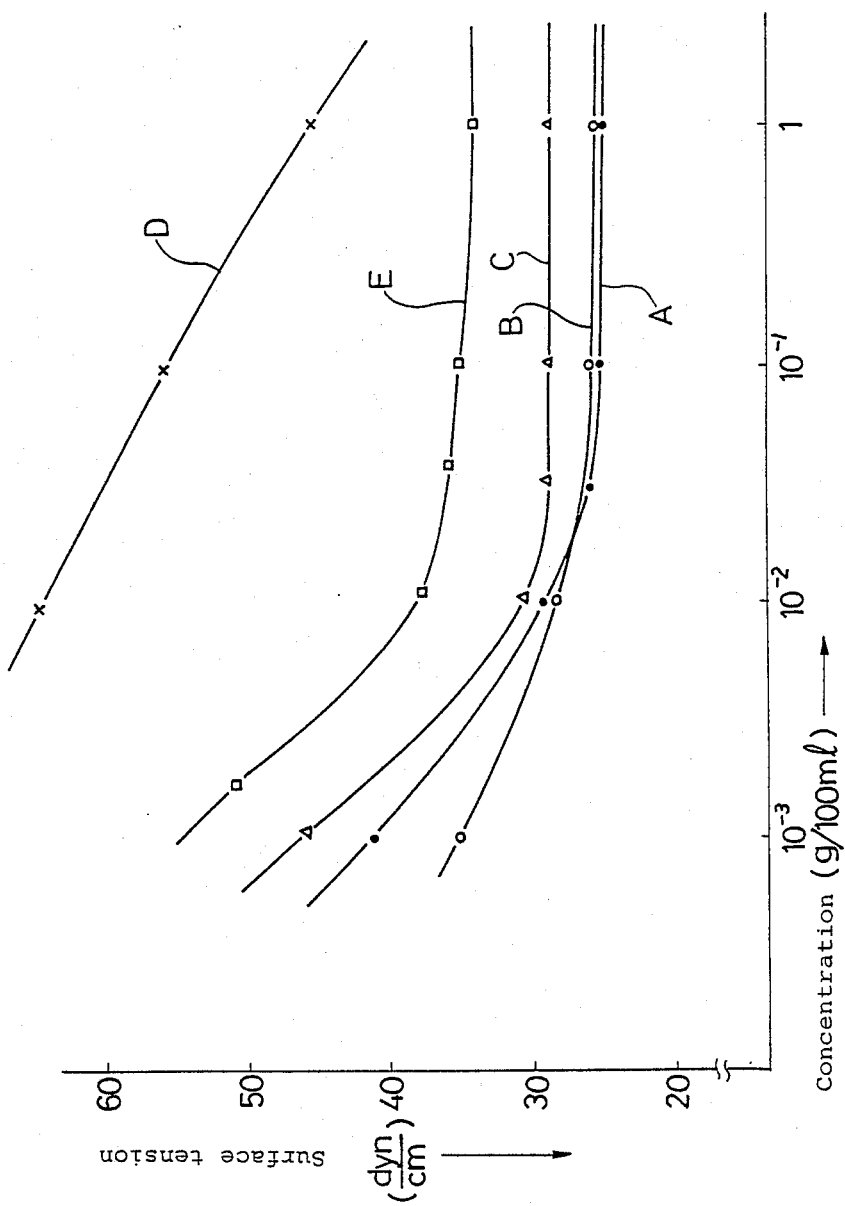

Then, using gelatin as a control, the surface tension characteristics (measured at 30° C.) of the proteinaceous emulsifiers obtained in Examples 18–20 and 22 are shown in FIG. 11. In this figure, the concentration-surface tension curve of the proteinaceous emulsifier obtained in Example 18 is denoted by A, that of the proteinaceous emulsifier obtained in Example 19 by B, that of the proteinaceous emulsifier obtained in Exaple 20 by C, that of gelatin by D, and that of the proteinaceous emulsifier obtained in Example 22 by E. By comparison of the curves A, B, C, D and E, it can be seen that the proteinaceous emulsifier obtained in Examples 18, 19 and 20 are markedly superior in surface activity to the proteinaceous emulsifier obtained in Example 22 and gelatin, and hence have excellent emulsifying power.

EXAMPLE 23 [PROTEINACEOUS EMULSIFIER 14]

A free L-alanine ester was prepared in manner described below and then used in an enzymatic reaction.

(Synthesis of a Free L-Alanine Ester)

4.46 g (0.05 mole) of L-alanine was taken, 11.4 g (0.06 mole) of p-toluenesulfonic acid hydrate was taken, and 11.79 g (0.055 mole) of myristyl alcohol was taken as an alcohol. After 200 ml of benzene was added thereto as a solvent, these materials were stirred and mixed well. The resulting reaction mixture was heated at the reflux temperature of benzene to carry out the esterification reaction. In this case, water was formed with the progress of the esterification reaction and released in the form of an azeotropic mixture with benzene, which was continuously removed from the reaction system. Thus, the reaction was completed in about 7–15 hours. After being cooled to room temperature, the reaction mixture was poured into a separating funnel and treated with 200 ml of a mixture of 0.2N NaOH and 3M NaCl solutions. This treatment was repeated three times. Thereafter, the benzene layer was isolated and washed thoroughly with water. After washing with water, the benzene layer was isolated and dried overnight over anhydrous sodium sulfate. After drying, the benzene layer was filtered and the resulting benzene solution was evaporated to remove the solvent. Thus, there was obtained 13.7 g (96% yield) of purified free L-alanine myristyl ester in the form of an oily material.

(Enzymatic Reaction)

120 ml of acetone was added to 480 ml of purified water and the resulting mixture was kept 37° C. with stirring. 120 g of gelatin as a hydrophilic protein and 34.26 g(i.e., 1 mole per 1,000 g of the gelatin) of L-alanine myristyl ester were added thereto and homogenized by adequate stirring. The resulting reaction mixture was adjusted to pH 9.0 with 1M $Na_2CO_3$.

After the addition of 1.05 g of L-cysteine hydrochloride monohydrate and 1.87 g of papain (manufactured by Nagase Sangyo K.K.), the aforesaid reaction mixture was stirred at 37° C. for 20 minutes. Then, the reaction was stopped by bringing the pH to 2.0 with 2N hydrochloric acid. The volume of the reaction mixture was about 1.5 liters.

While being kept at about 40° C., this reaction mixture was fed to a hollow-fiber ultrafiltration device (using a Cuprofan membrane and having an internal fiber diameter of 200μ, a membrane thickness of 11μ and an effective membrane area of 1.5 m$^2$) at a flow rate of about 10 ml/min. As the outer fluid, warm water at about 40° C. was fed at a flow rate of about 1 liter/min. After completion of the dialysis, the internal pressure of the same hollow-fiber ultrafiltration device was adjusted to about 2 kg/cm$^2$ and the dialyzed solution was concentrated under the same conditions as described above. Finally, about 300 ml of a concentrated solution was obtained.

This concentrated solution was dried with a spray dryer to obtain Proteinaceous Emulsifier 14.

EXAMPLE 24 [PROTEINACEOUS EMULSIFIERS 15, 16 AND 17]

Free L-leucine myristyl ester, L-glycine myristyl ester and L-isoleucine myristyl ester were prepared in the same manner as in Example 23.

Then, using these esters, enzymatic reactions were carried out in the same manner as in Example 23 to obtain Proteinaceous Emulsifiers 15, 16, and 17, respectively.

Emulsifying power was comparatively evaluated on Proteinaceous Emulsifier 14, 15 and 16 obtained in the above-described Examples 23 and 24. These proteinaceous emulsifiers were composed of decomposition products of gelatin having a carboxyl end group joined to L-alanine myristyl ester, L-leucine myristyl ester and L-glycine myristyl ester, respectively, by amide linkage.

(Procedure for Evaluation of Emulsifying Power)

1.8 parts by weight of liquid paraffin and a combined amount of 6.2 part by weight of a proteinaceous emulsifier and a 50 mM phosphate buffer solution (pH 7.0) were mixed so as to give a proteinaceous emulsifier concentration of 1%, 3% or 5%. Using an ultradisperser, the resulting mixture was homogenized at 9,000 rpm at 80° C. for one minute and then cooled to room temperature. The sample so prepared was diluted 1:200 with water and the absorbance of the diluted solution was measured with a spectrophotometer (Shimazu MPS-200).

Figure 12:
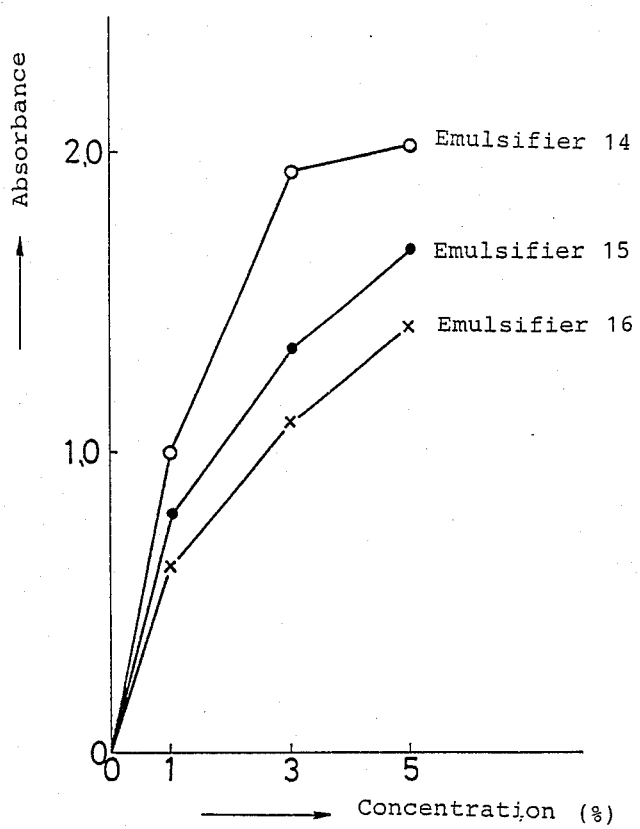
FIG. 12 is a diagram showing the relationship between emulsifier concentration and absorbance (i.e., emulsifying power) for several emulsifiers in accordance with the present invention which are composed of decomposition products of gelatin having the myristyl ester of leucine, alanine or glycine joined thereto by amide linkage.

The results thus obtained are shown in FIG. 12. As can be sent from this figure, the emulsifying power of Emulsifier 14 (L-alanine myristyl ester/gelatin), Emulsifier 15 (L-leucine myristyl ester/gelatin) and Emulsifier 16 (L-glycine myristyl ester/gelatin) decreases in that order.

EXAMPLE 25 [PROTEINACEOUS EMULSIFIER 18]

A free L-tyrosine ester was prepared in manner described below and then used in an enzymatic reaction.

(Synthesis of a Free L-Tyrosine Ester)

9.1 g (0.05 mole) of L-tyrosine was used, 11.4 g (0.06 mole) of p-toluenesulfonic acid hydrate was used, and 11.79 g (0.055 mole) of myristyl alcohol was used as an alcohol. After 200 ml of toluene was added thereto as a solvent, these materials were stirred and mixed well. The resulting reaction mixture was heated at the reflux temperature of toluene to carry out the esterification reaction. In this case, water was formed with the progress of the esterification reaction and released in the form of an azeotropic mixture with toluene, which was continuously removed from the reaction system. Thus, the reaction was completed in about 7-15 hours. After being cooled to room temperature, the reaction mixture was poured into a separating funnel and treated with 200 ml of a mixture of 0.2N NaOH and 3M NaCl solutions. This treatment was repeated three times. Thereafter, the toluene layer was isolated and washed thoroughly with water. After washing with water, the toluene layer was isolated and dried overnight over anhydrous sodium sulfate. After drying, the toluene layer was filtered and the resulting toluene solution was evaporated to remove the solvent. Thus, there was obtained 15.1 g (80% yield) of purified free L-tyrosine myristyl ester in the form of an oily material.

Figure 13:
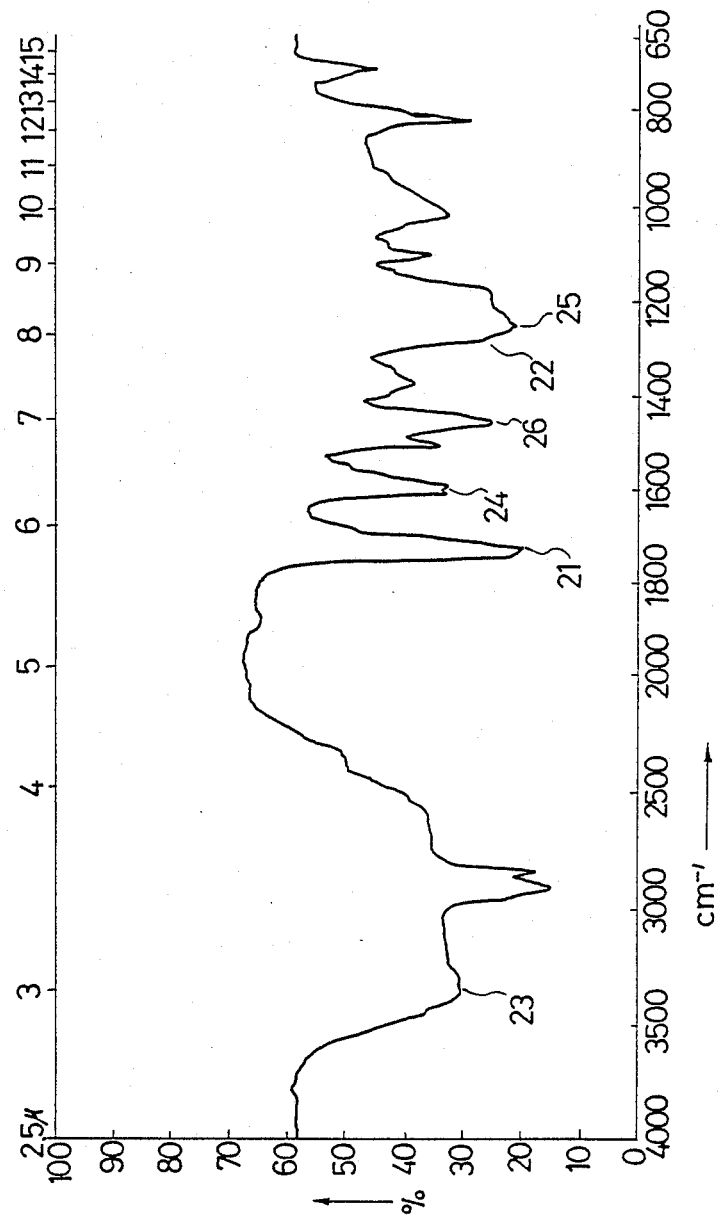
FIG. 13 is an infrared absorption spectrum of a proteinaceous emulsifier in accordance with the present invention.

An infrared absorption spectrum of the free L-alanine cetyl ester thus obtained is shown in FIG. 13. In this figure, the peaks 21 and 22 indicate the C=O stretching and C—O stretching vibrations originating from the ester linkage.

The peaks 23, 24 and 25 indicate the NH stretching, NH deformation and C—N stretching vibrations, respectively, of a primary amine. The peak 17 indicates the CH deformation vibration.

(Enzymatic Reaction)

120 ml of acetone was added to 480 ml of purified water and the resulting mixture was kept at 37° C. with stirring. 120 g of gelatin as a hydrophilic protein and 45.3 g (i.e., 1 mole per 1,000 g of the gelatin) of L-tyrosine myristyl ester were added thereto and homogenized by adequate stirring. The resulting reaction mixture was adjusted to pH 9.0 with 1M Na$_2$CO$_3$.

After the addition of 1.05 g of L-cysteine hydrochloride monohydrate and 1.57 g of papain (manufactured by Nagase Sangyo K.K.), the aforesaid reaction mixture was stirred at 37° C. for 20 minutes. Then, the reaction was stopped by bringing the pH to 2.0 with 2N HCl. The volume of the reaction mixture was about 1.5 liters.

While being kept at about 40° C., this reaction mixture was fed to a hollow-fiber ultrafiltration device (using a Cuprofan membrane and having an internal fiber diameter of 200μ, a membrane thickness of 11μ and an effective membrane area of 1.5 m$^2$) at a flow rate of about 10 ml/min. As the outer fluid, warm water at about 40° C. was fed at a flow rate of about 1 liter/min. After completion of the dialysis, the internal pressure of the same hollow-fiber ultrafiltration device was adjusted to about 2 kg/cm$^2$ and the dialyzed solution was concentrated under the same conditions as described above. Finally, about 800 ml of a concentrated solution was obtained.

This concentrated solution was dried with a spray dryer to obtain Proteinaceous Emulsifier 18.

We claim:

1. An emulsion type cosmetic composition comprising an oil phase and an aqueous phase, said composition containing, as the emulsifier, a proteinaceous emulsifier composed of (1) a decomposition product of a hydrophilic protein, said decomposition product having a carboxyl end group, said carboxyl end group of said decomposition product being joined to (2) the amino group of an amino acid ester by an amide linkage, said amino acid ester having an alcohol residue containing 14 to 22 carbon atoms.

2. An emulsion type cosmetic composition as claimed in claim 1 wherein said amino acid ester is an amino acid ester represented by the general formula $$R_3CH(NH_2)COOR_2 \qquad (2)$$

where $R_3$ is a methyl, isopropyl, n-butyl, isobutyl, sec-butyl, 1-hydroxyethyl, benzyl or p-hydroxybenzyl group and $R_2$ is a saturated aliphatic hydrocarbon radical or unsaturated aliphatic hydrocarbon radical having 14 to 22 carbon atoms.

3. An emulsion type cosmetic composition as claimed in claim 1 wherein said amino acid ester is an aliphatic alcohol ester of alanine represented by the general formula $$\underset{NH_2}{CH_3CHCOOR_4} \qquad (3)$$

where $R_4$ is a saturated aliphatic hydrocarbon radical or an unsaturated aliphatic hydrocarbon radical having 14 to 22 carbon atoms.

4. An emulsion type cosmetic composition as claimed in claim 1 wherein said amino acid ester is an aliphatic alcohol ester of leucine represented by the general formula $$\begin{array}{c}CH_3\\ \phantom{CH}\diagdown\\ \phantom{CH_3}CH-CH_2-\underset{NH_2}{CH}-COOR_5\\ \phantom{CH}\diagup\\ CH_3\end{array} \qquad (4)$$

where $R_5$ is a saturated aliphatic hydrocarbon radical or an unsaturated aliphatic hydrocarbon radical having 14 to 22 carbon atoms.

5. An emulsion type cosmetic composition as claimed in claim 1 wherein said amino acid ester is obtained by reacting an L-amino acid with an aliphatic alcohol.

6. An emulsion type cosmetic composition as claimed in claim 1 wherein said hydrophilic protein is casein, gelatin, sericin, soluble collagen or zein.

7. A cosmetic composition as claimed in claim 6 in which said decomposition product is an enzymatic decomposition product of said hydrophilic protein.

8. An emulsion type cosmetic composition as claimed in claim 1, where the decomposition product is an enzymatic decomposition product obtained by contacting said protein with an endopeptidase.

9. An emulsion type cosmetic composition as claimed in claim 8, where the endopeptidase is a thiol protease.

10. An emulsion type cosmetic composition as claimed in claim 9, where the thiol protease is one or more selected from the group consisting of papain, ficin, cathepsin B, kiwi fruit protease, bromelain, chymopapain, cathepsin L, yeast proteinase B, cathepsin S and TZ-peptidase.

11. An emulsion type cosmetic composition as claimed in claim 9 where the thiol protease is papain.

12. An emulsion type cosmetic composition as claimed in claim 1 containing from 1 to 2% by weight of said emulsifier.

13. A cosmetic composition as claimed in claim 1 wherein said amino acid ester is an amino acid ester represented by the general formula $$R_1CH(NH_2)COOR_2 \qquad (1)$$

where $R_1$ is hydrogen, an alkyl group, an ω-hydroxyalkyl group, an aralkyl group or an ω-hydroxyaralkyl group and $R_2$ is a saturated hydrocarbon or unsaturated hydrocarbon radical having 14 to 22 carbon atoms.

* * * * *